United States Patent
McKersie et al.

(10) Patent No.: US 6,518,486 B1
(45) Date of Patent: Feb. 11, 2003

(54) ENHANCED STORAGE ORGAN PRODUCTION IN PLANTS

(75) Inventors: Bryan D McKersie, Apex, NC (US); Stephen R Bowley, Guelph (CA); Kim S Jones, Toronto (CA); Karen Samis, Guelph (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/329,550

(22) Filed: Jun. 10, 1999

Related U.S. Application Data

(60) Provisional application No. 60/089,197, filed on Jun. 12, 1998.

(51) Int. Cl.[7] .................. A01H 5/00; C12N 15/82
(52) U.S. Cl. ................. 800/298; 435/320.1; 435/375; 435/468; 800/278; 800/287
(58) Field of Search .................... 435/320.1, 375, 435/468, 69.1; 800/278, 287, 290, 298

(56) References Cited

U.S. PATENT DOCUMENTS

| | | | |
|---|---|---|---|
| 5,436,393 A | * 7/1995 | Rocha-Sosa et al. | |
| 5,436,394 A | 7/1995 | Willmitzer et al. | 800/284 |
| 5,554,530 A | 9/1996 | Fortin et al. | 435/256.8 |
| 5,618,988 A | * 4/1997 | Hauptmann et al. | |
| 5,639,950 A | * 6/1997 | Verma et al. | |
| 5,659,026 A | 8/1997 | Baszczynski et al. | 800/288 |
| 5,723,757 A | * 3/1998 | Rocha-Sosa et al. | |
| 5,750,869 A | 5/1998 | Shewmaker | 435/411 |
| 5,821,398 A | 10/1998 | Speirs et al. | 800/301 |
| 5,824,798 A | 10/1998 | Tallberg et al. | 536/128 |
| 5,837,848 A | * 11/1998 | Ely et al. | |
| 5,837,876 A | 11/1998 | Conkling et al. | 800/293 |
| 5,855,881 A | * 1/1999 | Loike et al. | |
| 5,856,467 A | 1/1999 | Hofvander et al. | 536/45 |
| 6,002,068 A | * 12/1999 | Privalle et al. | |

FOREIGN PATENT DOCUMENTS

| | | | |
|---|---|---|---|
| EP | 0 356 061 | 2/1990 | |
| EP | 0 359 617 | 3/1990 | |
| WO | WO 90/02804 | 3/1990 | |
| WO | WO 94/13797 | 6/1994 | C12N/15/11 |
| WO | WO 98/03631 | 1/1998 | |

OTHER PUBLICATIONS

McKersie et al (1993) Plant. Physiol. 103:1155–1163.*
McKersie et al (1996) Plant Physiol. 111:1177–1181.*
Aono et al (1995) Plant Cell Physiol. 36:1687–1691.*
McKersie et al (1997) Acta Physiologiae Plantarum 19: 485–495.*
Burdick et al (1990) Journal of Experimental Botany 41:223–228.*
Tanaka, K. et al, "Stress tolerance of transgenic Nicotiana tabacum with enhanced activities of glutathione reduciase and superoxide diamolase", Biochemical Society Transactions 200S:24 (1996)–XP–002118433.
Breusegem, F. et al., "Overproduction of Arabidopsis thaliana FeSOD Confers Oxidatives Stress Tolerance to Transgenic Maize", Plant Cell Physiol. 40(5):515–523 (1999)–XP–002118436.
Bowley and McKersie, "Relationships among freezing, low temperature flooding, and ice encasement tolerance in alfalfa," Can. J. Plnt Sci., 70:227–235, 1990.
McKersie et al., "Water–deficit tolerance and field performance of transgenic alfalfa overexpressing superoxide dismutase," Plant Physiol., 111:1177–1181, 1996.
McKersie et al., "Winter survival of transgenic alfalfa overexpressing superoxide dismutase," Plant Physiol. 119:839–847, 1999.
McKersie et al., "Superoxide dismutase enhances tolerance of freezing stress in transgenic alfalfa (Medicago sativa L.)," Plant Physiology, 103:1155–1163, 1993.
McKersie et al., "Manipulating freezing tolerance in transgenic plants," Acta Physiol. Plant, 19:485–495, 1997.

* cited by examiner

Primary Examiner—James Ketter
Assistant Examiner—Bronwen M. Loeb
(74) Attorney, Agent, or Firm—Howrey Simon Arnold & White, LLP

(57) ABSTRACT

A method for increasing the mass of a storage organ of a plant comprising tansforming the plant with at least one heterologous gene that encodes an enzyme that results in NAD(P)H consumption is disclosed. Preferably the method comprises transforming the plant with a gene that encodes an enzyme that is directly involved in NAD(P)H consumption. Such plants are characterized as having an increase in the mass of the storage organs. The enzymes include but are not limited to alcohol dehydrogenase, glutathione reductase, dehydroascorbate reductase, monodehydroascorbate reductase, mitochondrial alternative oxidase, NADH oxidase and NADPH oxidize. Vector and transformed plants are also disclosed.

62 Claims, 19 Drawing Sheets

T-DNA OF pMitSOD (pSOD1, pEX1SOD) BINARY VECTOR

ENHANCED STORAGE ORGAN PRODUCTION IN PLANTS

This application claims priority to U.S. provisional patent application serial No. 60/089,187, filed Jun. 12, 1998, the entirety of which is incorporated herein by reference.

FIELD OF THE INVENTION

The invention relates to genetically transformed plants that develop larger storage organs. More specifically this invention relates to plants comprising a heterologous gene encoding an enzyme involved in NAD(P)H consumption. These plants develop larger roots, exhibit increased growth, and increased stress tolerance.

BACKGROUND OF THE INVENTION

Perennial crops, including many forage crops, persist in cultivated fields for several years. Because these plants are capable of multiple cycles of regrowth and harvest, the growth and development are distinctly different than annual grain crops. In most perennial forage production systems, for example alfalfa (*Medicago sativa*), plants are defoliated before any seed is produced and, unlike annual crops, regrow new vegetative shoots from crown or axillary buds. The energy, carbon, nitrogen and other reserves necessary to support this regrowth come from the root system and crown. The reserves in the root and crown are depleted as the new shoots develop new leaves, which capture light energy for photosynthesis. At a certain stage of development the shoot becomes self-sufficient and obtains its energy and carbon requirements from photosynthesis. At a later stage, the shoot has excess energy and carbon from photosynthesis and exports the excess to the root and crown system to support nitrogen fixation, nutrient uptake and replenishment of reserves. Replenishment of reserves continues until the plant is defoliated again by either grazing, harvesting or natural stresses, for example, freezing.

Roots or other storage organs of most forage legumes convert the imported sucrose to starch, whereas forage grasses store fructans. The rate of starch or fructan accumulation in these storage organs is usually not controlled by the supply of sucrose from the leaf. Instead, sink strength is determined by the ability of the storage organ to synthesize and store starch or fructans. This is determined in turn by the number of amyloplasts (sites of starch storage) in the cell, the number of storage cells in the root, and the metabolism of the cell.

The size of the root system and the quantity of stored nutrient reserves that are available to support new shoot growth determines the rate and amount of shoot regrowth and the economic yield of perennial plants. The agronomic management of forage crops for example is specifically designed to maximize the quantities of these reserves that may accumulate between harvests (Hanson et al., 1988; Barnes et al., 1995). The quantity of stored nutrient reserves determines the ability of the plant to survive winter. Therefore, in northern climates, crop production recommendations include clear guidelines to avoid harvesting alfalfa and other forage crops during late summer and early autumn because these reserves are being replenished for winter The performance index of alfalfa for example after several winter stresses has been related to the size of the roots. Significant correlations of root mass were found with performance after flooding and icing stress, and a correlation (not significant at the 5% level) was found with freezing stress (Bowley and McKersie, 1990). Poot size alone appears to have an effect on the performance of alfalfa following winter.

Therefore, there is a need to increase the sink strength of the roots of plants. Increased sink strength would increase the amount of carbohydrate and other stored nutrients in roots or other storage organs. The increased levels of reserves would increase the regrowth rate, yield potential, and the likelihood that a perennial plant would survive winter. Similarly, increased reserve levels would ensure yield potential of an annual under varying environmental conditions.

Genetic transformation has been previously used to modify source-sink relationships in plants. Although attempts to improve photosynthesis and thereby increase the export of sucrose to sink organs have not been successful, the modification of carbohydrate metabolism in the sink organ has increased the size of potato tubers. U.S. Pat. No. 5,436,394 discloses the modification of the distribution of photoassimilates, including sucrose, in transgenic potato plants that expressed a yeast invertase in either the cytosol or apoplast of tubers. Cytosolic localization gave rise to a reduction in tuber size and an increase in tuber number per plant whereas apoplastic targeting led to an increase in tuber size and a decrease in tuber number per plant. Several plants exhibited phenotypes comprising reduced internode distances and severly reduced root growth.

U.S. Pat. No. 5,723,757 discloses the use of a patatin promoter to drive the expression of gene of interest within a sink organ, such as a root, within transgenic plants. In U.S. Pat. No. 5,750,869, transgenic plants that ectopically express sucrose phophate synthase are shown to exibit altered sink capacities, with increased levels of sucrose, starch and cellulose observed within the sink tissue. Neither of these documents observed increased root growth, or root size, in the transformed plants. Furthermore, the ability of the transgenic plant to withstand stresses WAS not contemplated.

In order to increase the sink strength and size of roots and other storage organs, it may be necessary to directly stimulate the growth and development of the organ. In WO 98/03631, increased growth of main and lateral roots was noted in Arabidopsis transformed with a nucleic acid encoding mitotic cyclin proteins, preferably the cyclaAt protein. However, there is no indication that these plants exhibited increased regrowth potential, nor that they had increased stress tolerance.

U.S. Pat. No. 5,554,530 discloses an increased tolerance to salt stress and drought resistance in plants transformed with δ-pyrroline-5-carboxylic synthetase. Transformed plants exhibited higher levels of proline and improved root growth under salt stress conditions. However, regrowth potential in pernnial plants was not considered. Other stress tolerant plants have been produced by transforming plants with superoxide dismutase (EP 359,617 and EP 356,061), however, no increase in root growth or root size was observed. The regrowth potential in perennial plants was also not considered.

U.S. Pat. No. 5,821,398 discloses the production of transgenic plants expressing alchohol dehydrogenase (ADH) under the control of a fruit specific, inducible promoter, preferably the tomato ADH2 promoter. Expression of ADH within fruits results in controlled fruit softening and increased flavor content.

In U.S. Pat. No. 5,855,881, the expression of mammalian ADH within plants to produce a ready source of ADH for use as a dietary supplement to ameliorate the effects of alcohol consumption in an animal is discussed. There is no teaching of producing plants expressing ADH that exhibit the properties of increased stress tolerance or increased regrowth potential.

It is an object of the invention to overcome disadvantages of the prior art. This object is met by the combinations of features of the main claims, the sub claims disclose further advantageous embodiments of the invention.

The present invention is directed to introducing at least one heterologous gene into a plant encoding an enzyme involved in consuming NAD(P)H, for example, but not limited to, alcohol dehydrogenase. These plants have increased storage organ mass, such as roots, and the sink strength of the plant is also increased. Furthermore, these plants exhibit increased stress tolerance, and exhibit increased regrowth potential, within and in perennial plants, between growth seasons.

SUMMARY OF THE INVENTION

This invention relates to genetically transformed plants that develop larger storage organs. More specifically this invention relates to plants comprising a heterologous gene encoding an enzyme involved in NAD(P)H consumption. These plants develop larger roots, exhibit increased growth, and increased stress tolerance According to the present invention there is provided a method of increasing the mass of a storage organ of a plant, comprising:

i) transforming the plant with at least one heterologous gene that encodes at least one enzyme that results in NAD(P)H consumption to produce a transformed plant;

ii) selecting the transformed plant for occurrence of the heterologous gene;

iii) growing the transformed plant.

Preferably, the heterologous gene encodes an enzyme that is directly involved in NAD(P)H consumption, selected from the group consisting of alcohol dehydrogenase, glutathione reductase, dehydroxyascorbate reductase, monodehydroascorbate reductase, mitochondrial alternative oxidase, NADH oxidase, and NADPH oxidase. However, the heterologous gene may also encode an enzyme indirectly involved in NAD(P)H consumption, selected from the group consisting of superoxide dismutase, ascorbate peroxidase, and dehydroxyascorbate reductase.

The present invention also pertains to a method for increasing the mass of a storage organ of a plant, comprising:

i) transforming the plant with two distinct heterologous genes that encode enzymes that results in NAD(P)H consumption to produce a transformed plant;

ii) selecting the transformed plant for occurrence of the heterologous genes;

iii) growing the transformed plant.

This invention also relates to a vector comprising a regulatory element in operative association with at least one heterologous gene, wherein the heterologous gene, when expressed in a plant, encodes an enzyme that consumes NAD(P)H and produces a transformed plant characterized in having increased storage organ mass. Preferably, the regulatory element is active in the storage organ, and is root specific.

Furthermore, this invention also relates to a vector comprising two regulatory elements in operative association with two distinct heterologous genes, wherein expression of the heterologous genes in a plant results in the plant having increased storage organ mass. At least one of the regulatory elements is active in the storage organ, and is root specific.

This invention is directed to a transgenic plant, transgenic plant cell, and transgenic seed comprising the either of the vectors defined above. The transgenic plant may be a perennial or an annual plant. If perennial, the plant is selected from the group consisting of strawberries, raspberries, grapevines, apple, roses, orchard grass, brome grass, timothy, ryegrass, fescue, alfalfa, clover, birdsfoot trefoil, turfgrass, bentgrass and bluegrass. If annual, the plant is a winter annual plant or a root crop selected from the group consisting of Brassica spp., wheat, barley, oats, rye, canola, maize, rice, barely, soybean, potatoes and Phaseolus spp The present invention embraces a method of increasing the tolerance to an environmental stress of a plant, comprising:

i) transforming the plant with at least one heterologous gene that encodes an enzyme that results in NAD(P)H consumption;

ii) selecting the transformed plant for occurrence of the heterologous gene;

iii) growing the transformed plant.

This method also pertains to increasing flooding, freezing, desication, or drought resistance or a combination thereof.

The invention includes an expression system for increasing the size of the storage organs of a plant or to impart greater sink strength in the storage organs, for example, including but not limited to roots, crowns, rhizomes, stolons, tubers, culmns, basal stems and tap roots. The invention also includes a transgenic plant, a plant part, a seed, a plant cell and a plant tissue that includes the expression system. The invention includes the use of the expression system to increase the size of storage organs and the sink strength of the plant.

This summary of the invention does not necessarily describe all necessary features of the invention but that the invention may also reside in a sub-combination of the described features.

DESCRIPTION OF THE DRAWINGS

Preferred embodiments of the invention will be described in relation to the drawings in which:

FIG. 2(A), ADH activity over a pH range of 6 to 9 in roots obtained from plants flooded for 24 hr. FIG. 2(B), ADH activity over pH 6 to 9 within aerobic roots. Control (♦) is N-4-4-2; (■) transgenic plant 3 (ADH-3-3), and (Δ) transgenic plant 5 (ADH-3-5).

FIG. 5(A) shows winter survival, indicated as stand counts as % of original. FIG. 5(B) shows herbage yield (g/m$^2$).

FIG. 6(A) shows the PCR products from the adh primers. Lanes 1 and 2 DNA from transgenic plants, lanes 3 and 4, negative control, lane 5, adh3 plasmid (positive control). FIG. 6(B) shows the PCR products from the bar primers. Lanes 3 and 4 DNA obtained from transgenic plants, lane 1, markers, lanes 5 and 6 negative control, lane 7 positive control (bar plasmid), lane 2, no sample. Similar results were obtained in all progeny and the results were used to separate the plants into two populations with and without the T-DNA insertion.

FIG. 20(A):Chl MnSOD (pSOD4) PCR amplification (700 bp band) FIG. 20(B):BAR (pADH3) PCR amplification (410 bp) (Samples are in same order on each gel). Lane 1:100 bp ladder; lanes 2–19 F1 progeny of C30; Lane 20: Parent N4 Chl MnSOD; Lane 21:Parent H19-8; Lane 22; H$_2$O control; Lane 23:100 bp ladder. Double Transgenics: Lanes 4, 5, 11, 16, 19; Progeny 30-4, 30-5, 30-11, 30-16, 30-20.

DESCRIPTION OF THE INVENTION

Figure 1:
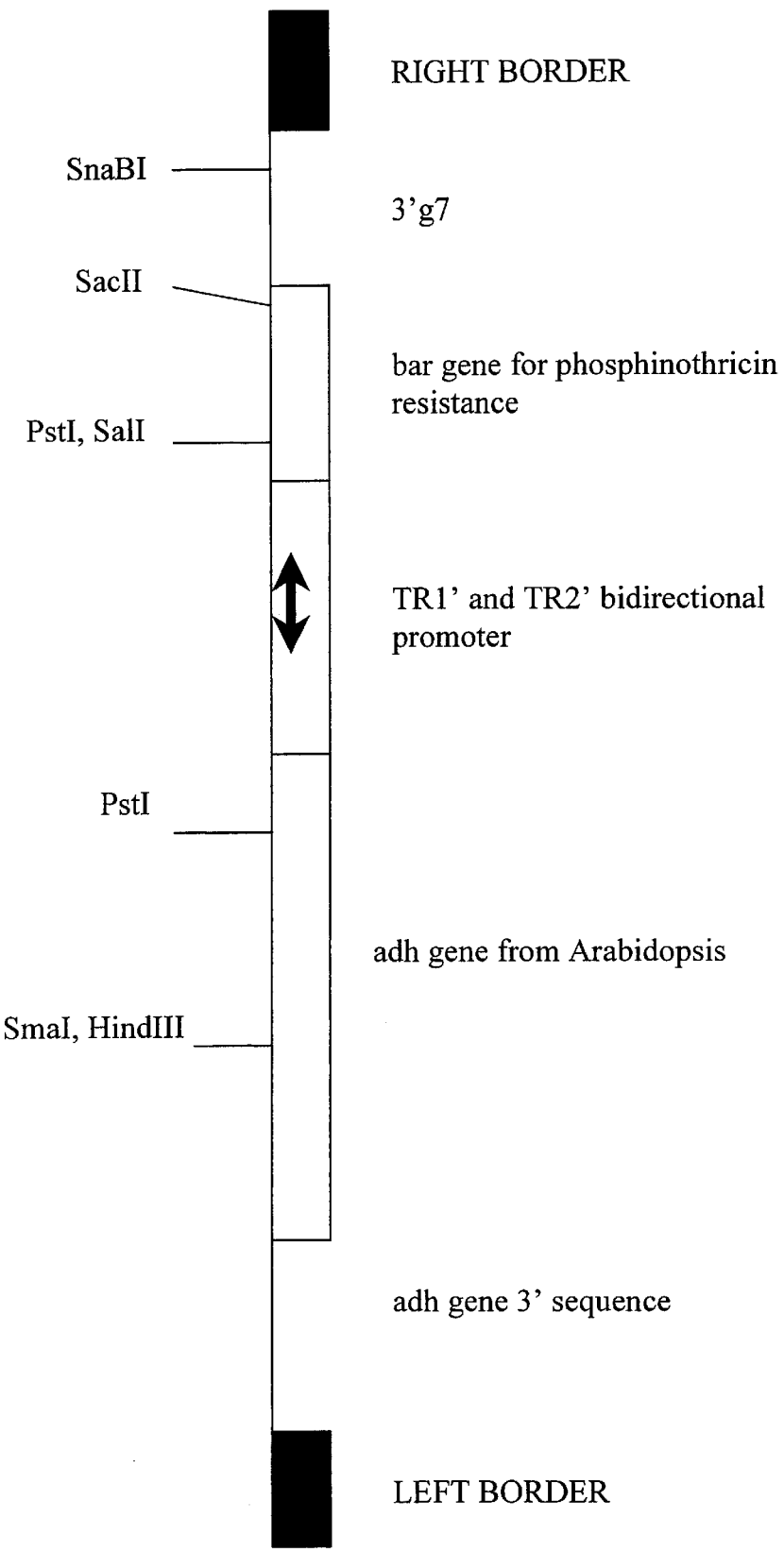
FIG. 1 shows a restriction map of the T-DNA region in pADH3 vector used to transform *Medicago sativa*.

The present invention relates to the expression of transgenes in storage organs of plants that alters the sink strength of storage organs such as the root. More specifically this invention relates to plants comprising a heterologous gene encoding an enzyme involved in NAD(P)H consumption. The size and mass of the storage organs is increased, and this increases the herbage yield, and for perennials and winter annuals, their persistence and longevity. In addition these plants exhibit increased stress tolerance.

The following description is of a preferred embodiment by way of example only and without limitation to the combination of features necessary for carrying the invention into effect.

Without wishing to be bound by theory, it is contemplated that the beneficial properties observed in these transgenic plants result from lowering the redox potential, defined as the NAD(P)H to NAD(P) ratio, within plant cells, or increasing the flux through the NAD(P)H pools. To increase the size of a plant's root system or any desired storage organ, it is necessary to introduce a modified gene to cause the cells of the desired tissue to have a lower steady-state redox potential. Alternately, it may be sufficient to increase the flux of NAD(P)H production by the stimulation of specific metabolic pathways. One strategy to accomplish this is to cause the cell to directly oxidize NADPH or NADH. An example of a gene that oxidizes NADO, which is not to be considered limiting in any manner, is alcohol dehydrogenase. Other examples are given below. An alternate strategy for lowering the steady-state redox potential of an organ is to indirectly decrease the redox potential within a cell, for example, but not limited to, increasing the production of ascorbate free radicals, oxidizing glutathione or increasing the utilization of NAD(P)H. Alternatively, it may be suffient to increase the flux of NAD(P)H production by the stimulation of specific metabolic pathways. However, other mechanisms may also account for the beneficial properties disclosed herein, that arise as a result of plants transformed with constructs that encode enzymes that consume NAD (P)H directly or indirectly.

The preferred transgene that is introduced into the plant produces an enzyme that modifies the metabolism of a desired storage organ, for example, but not limited to the root, to increase its consumption of NADH or NADPH, possibly modifying the cell's redox potential, and increasing the flux through the NAD(P)H pool. Examples of enzymes that may be used for this purpose include, but are not limited to, the following:

alcohol dehydrogenase
superoxide dismutase
ascorbate peroxidase
glutathione reductase
dehydroascorbate reductase
monodehydroascorbate reductase
mitochondrial alternative oxidase
NADH oxidase
NADPH oxidase
Glutathione peroxidase The above transgenes may be expressed singly or in various combinations in a tissue specific manner, for example within plant roots or storage organs. Preferably, the selected transgene encodes alcohol dehydrogenase (ADH), or a combination of ADH and another desired transgene that consumes NAD(P)H either directly or indirectly The enzyme alcohol dehydrogenase (E.C. 1.1. 1) is non-specific and reversible. This is the terminal reaction in fermentation or anaerobic respiration through glycolysis. thgis enzyme converts an aldehyde, for example acetaldehyde, to an alcohol, for example ethanol, using reducing equivalents from NADH, however, the enzyme is fully reversible and also converts an alcohol to an aldehyde, generating NADH ADH is considered to be an anaerobic peptide because transcription is enhanced in anaerobic or hypoxic growth conditions. ADH may be obtained from any source and used as described herein, however, preferably the ADH is of plant origin.

By "regulatory element" it is meant those that include developmentally regulated, tissue specific, inducible and constitutive regulatory elements. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within the plant as well, such regulatory elements are also considered "tissue specific". It is to be understood that tissue specific regulatory elements may also be preferentially active within a tissue throughout development, and exhibit a basal level of activity in other organs. Regulatory elements may be found either upstream, within, downstream or a combination thereof, of the coding region of a gene.

An inducible regulatory element is one that is capable of directly or indirectly activating transcription of one or more DNA sequences or genes in response to an inducer. In the absence of an inducer the DNA sequences or genes will not be transcribed. Typically the protein factor, that binds specifically to an inducible regulatory element to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

A constitutive regulatory element directs the expression of a gene throughout the various parts of a plant and continuously throughout plant development. Examples of known constitutive regulatory elements include promoters associated with the CaMV 35S transcript. (Odell et al., 1985, *Nature,* 313: 810–812), the rice actin 1 (Zhang et al, 1991, *Plant Cell,* 3: 1155–1165) and triosephosphate isomerase 1 (Xu et al, 1994, *Plant Physiol.* 106; 459–467) genes, the maize ubiquitin 1 gene (Cornejo et al, 1993, *Plant Mol. Biol.* 29: 637–646), the Arabidopsis ubiquitin 1 and 6 genes (Holtorf et al, 1995, *Plant Mol. Biol* 29: 637–646), and the tobacco translational initiation factor 4A gene (Mandel et al, 1995 *Plant Mol. Biol.* 29: 995–1004).

The expression of a transgene of the present invention is controlled by a regulatory element as defined above. Preferably, the regulatory element enables transcription in a tissue specific manner, within root or storage organ cells. Examples of root specific regulatory elements include, but are not limited to the bidirectional promoter TR1' and TR2' (Velten et al 1984), or other regulatory elements known to be expressed in a root specific manner (e.g. Tingey et al., EMBO J. 6:1, 1987; An et al., Plant Physiol. 88:547, 1988; Oppenheimer et al., Gene 63:87, 1988; Conkling et al., Plant Physiol. 93:1203, 1990; Ohl et al., Cell 2:837, 1990; van der Zaal et al., Plant Mol. Biol. 16:983, 1991), or those disclosed in U.S. Pat. Nos. 5,436,393, 5,837,848, 5,837,876, 5,659,026, 5,856,467, 5,824,798, 5,837.848, and 5,837,876. However, regulatory elements may be employed that result in transcription ill other tissues and organs, or that are induced by external stimuli.

The chimeric gene construct of the present invention, comprising at least one desired transgene and at least one regulatory element, can filter comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Examples of suitable 3' regions are the 3' transcribed non-translated regions containing a polyadenylation signal of Agrobacterium tumor inducing (Ti) plasmid genes, such as the nopaline synthase (Nos gene) and plant genes such as the soybean storage protein genes and the small subunit of the ribulose-1,5-bisphosphate carboxylase (ssRUDISCO) gene. The 3' untranslated region from the structural gene of the present construct can therefore be used to construct chimeric genes for expression in plants.

The chimeric gene construct of the present invention can also include enhancers, either translation or transcription enhancers, as may be required. These enhancer regions are well known to persons skilled in the art. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

The transgene of the present invention may further comprise a transit peptide sequence that targets the peptide to accumulate in a specific subcellular compartment or membrane system in the root or storage organ cell such as the cytosol, mitochondria, apoplasm, plastic, or plasmalemma. Such transit sequences are well known to one of skill in the art.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like, or phosphinothricin resistance, for example the bar gene. Similarly, enzymes providing for production of a compound identifiable by colour change such as GUS (β-glucuronidase), fluorescence, or luminescence, such as luciferase are useful.

Also considered part of this invention are transgenic plants containing a chimeric gene construct of the present invention comprising a desired transgene in operative association with a regulatory element. Methods of regenerating whole plants from plant cells are known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. The constructs of the present invention can be introduced into plant cells using Ti plasmids, Ri plasmids, plant virus vectors, direct DNA transformation, micro-injection, electroporation, biolistics etc. For reviews of such techniques see for example Weissbach and Weissbach, *Methods for Plant Molecular Biology*, Academy Press, New York VIII, pp. 421–463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langgmans Ltd. London, pp. 561–579 (1997). The present invention further includes a suitable vector comprising the transgene or the chimeric gene construct.

Suitable plants that may benefit from the transgenes disclosed herein include both perennial and annual plants that are grown for a variety of reasons. Examples of perennial plants that are grown for forage and repeatedly harvested by defoliation include, but are not limited to:

legumes, for example, alfalfa, clover, birdsfoot trefoilgrasses;

grasses, for example orchardgrass, bromegrass, timothy, ryegrass, fescue.

Other perennial plants include those that are grown for fruit and for ornamental or recreational purposes such as but not limited to:

fruit crops, for example, strawberry, raspberry, grapevines, apple;

turfgrass, for example, ryegrass, bentgrass, fescue, bluegrass;

flowers, for example roses.

Annual plants and winter annual plants that are grown for forage or seed can also be transformed in accordance with the present invention. These plants include, but are not limited to:

cereals, for example, wheat, barley, oats, rye;

Brassica spp. for example, canola.

Annual plants that are grown for forage or seed may also benefit from the methods disclosed herein. These plants include:

cereals, for example, maize, wheat, rice and barley;

legumes, for example, soybean and Phaseolus spp.

It is to be understood that wheat, barley oats and canola include all types or varieties of wheat, barley, oats and canola.

Root crops exhibiting larger root growth and increased stress tolerance may also be produced using the constructs and methods as described herein. Such plants include, but are not limited to:

carrots, turnips, ginseng, potatoes, sugarbeet and cassava.

The above description is not intended to limit the claimed invention in any manner, furthermore the discussed combination of features might not be absolutely necessary for the inventive solution.

While this invention is described in detail with particular reference to preferred embodiments thereof, the embodiments are offered to illustrate but not limit the invention.

EXAMPLE 1

Preparation of *Medicago sativa* Transformed with ADH

The enzyme alcohol dehydrogenase (ADH; E.C. 1.1.1.1) converts acetaldehyde to ethanol using reducing equivalents from NADH. This is the terminal reaction in fermentation or anaerobic respiration through glycolysis. The enzyme is fully reversible and is considered to be an anaerobic peptide because transcription is enhanced in anaerobic or hypoxic growth conditions. ADH is a non-photosynthetic enzyme. Without wishing to be bound by theory, because ADH oxidizes NADH in this reaction, the redox potential, or redox flux, of the plant cell will be reduced and this may restrict the activity of monodehydroascorbate reductase and other enzymes that metabolize hydrogen peroxide or NADH under conditions when NADH is limiting. ADH may therefore act directly within the root to lower the redox potential in the root and increase the mass of the root.

The adh gene from *Arabidopsis thaliana* was described by Chang and Meyerowitz (1986) To remove the promoter from adh, a BamHl restriction site was inserted prior to the ATG start codon by M13 site specific mutagenesis to give the sequence . . . ATC GGA TCC ATG TCT . . . (SEQ ID NO:1). The gene was isolated as a BamHl fragment and inserted into a binary transformation vector pDB2 12 that is related to pGV94 1 described by DeBlaere et al. (1987) The binary vector pADH3 contains the bar gene coding for phosphinothricin resistance (DeBlock et al. 1987) and the neo gene under the control of the bidirectional promoter sequence TR1= and TR2' (Velten et al. 1984), respectively. pDB212 was digested with ClaI, HindIII to remove the neo gene and pADH2 was digested with BamHl to remove the adh gene; both were treated with Klenow reagent to remove single stranded regions and ligated to form pADH3 (FIG. 1). This plasmid contains the bar gene under the control of the Tr1' promoter as a selectable marker, and the Arabidopsis adh gene under the control of the TR2' promoter. However, other promoters can be used to express the ADH gene in a tissue specific manner plants according to the present invention.

The binary vector pADH3 was transferred to *Agrobacterium tumefaciens* C58C1 Rif pMP90 by triparental mating. Alfalfa (*Medicago sativa* L.) clone RA3 was transformed as previously described (D'Halluin et al. 1990). Putatively transgenic plants were regenerated and screened for resistance to phosphinothricin and expression of PAT activity from the bar gene (DeBlock et al. 1987). Occurrence of the transgene within plants was verified via Southern or PCR analysis (see below, Example 8). Only plants exhibiting tolerance and positive marker activity were transplanted to soil.

EXAMPLE 2

Expression of ADH Activity in Roots

Figure 2A:
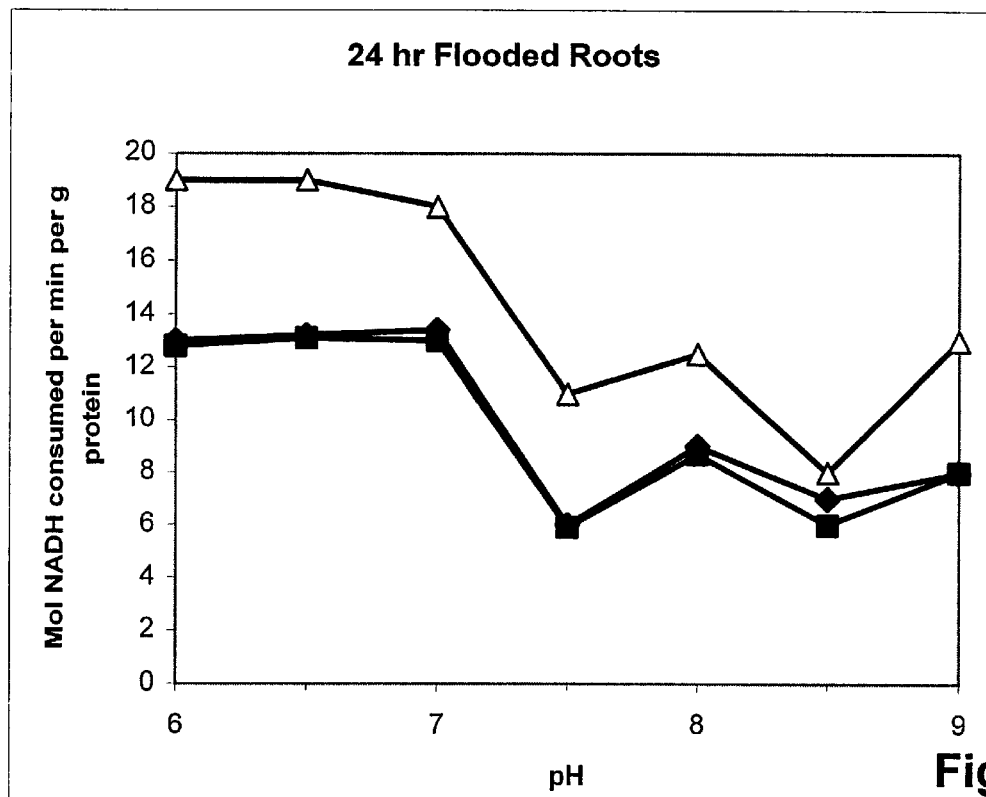
FIGS. 2A and 2B show alcohol dehydrogenase activity (ADH) in flooded and aerobic roots of three alfalfa plants.
Figure 2B:
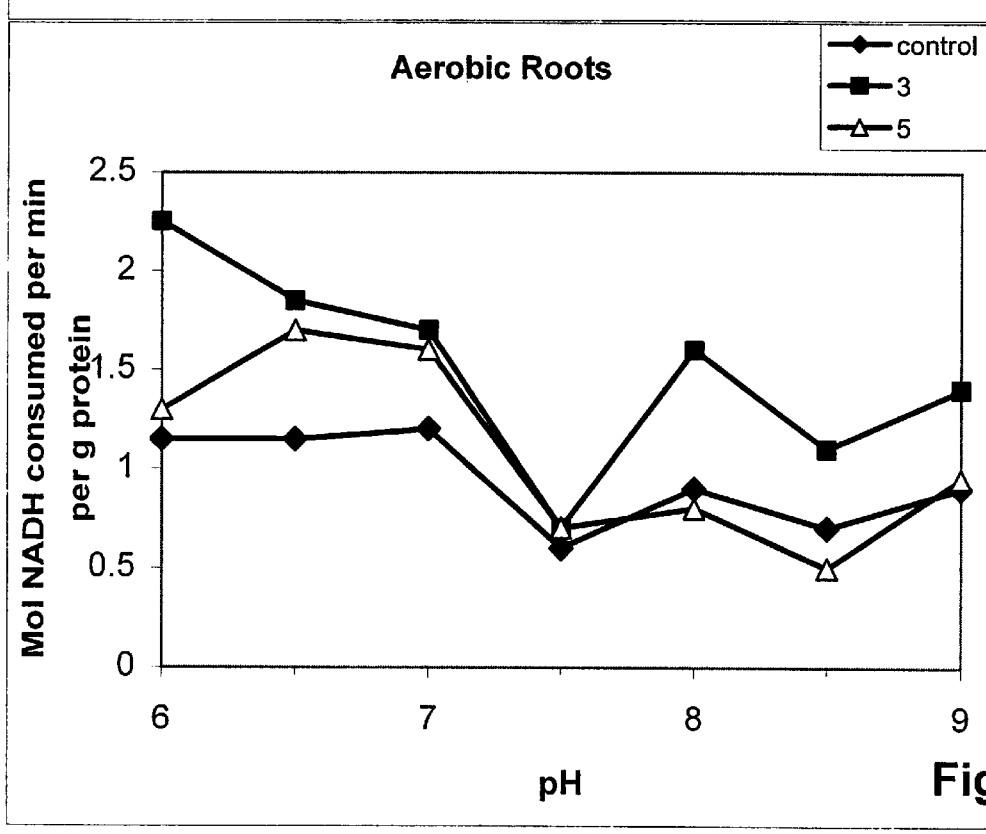

ADH activity in extracts of alfalfa roots was resolved into three distinct forms based pH optima for the reduction of acetaldehyde. One form of ADH had a broad optima from pH 6 to 7. A second had maximum activity at pH 8 and a third at pH 9. The same three forms were present in two transgenic alfalfa plants, which had similar activities when the roots were maintained aerobic. When flooded for 24 h (see Flooding Tolerance), the three forms of ADH increased in activity approximately 10 fold in all plants. Transgenic plant 5 (ADH-3-5) had higher activity than the control, but the flooding tolerant transgenic 3 (ADH-3-3) did not have higher ADH activity at any pH (FIG. 2).

Figure 3:
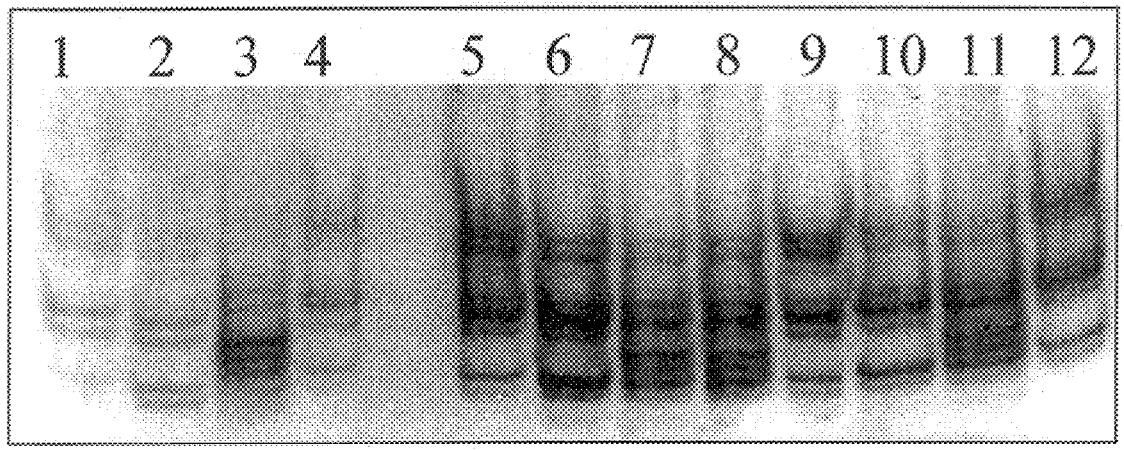
FIG. 3 shows native PAGE of alfalfa root extract stained for alcohol dehydrogenase. Lanes 1–4: no flooding treatment; lanes 5–8: 24 h flooding; lanes 9–12: 48 h flooding; lanes 1, 5 and 9: control N4-4-2; lanes 2, 6, and 10: transgenic 3 (ADH-3-3); lanes 3, 7, and 11: transgenic 4 (ADH-3-4); lanes 4, 8 and 12: transgenic 5 (ADH-3-5).

ADH in the extracts from non-transgenic alfalfa roots could be resolved into eight isozymes by native PAGE (FIG. 3). When the roots were flooded for 24 h (see Example 4), the isozyme banding pattern did not change dramatically and the activity of all isozymes increased. Similarly, in the three transgenic plants, the ADH isozyme banding pattern was not altered by the anaerobic treatment. In transgenic plant 3 (ADH 3-3), which exhibited enhanced flooding tolerance, there were no new ADH isozymes detected in the root extracts. The relative intensity of isozymes 6, 7, and 8 decreased whereas the activity of isozymes 1 and 2 had increased. There were additional ADH isozymes in the root extracts from transgenic plants 4 (ADH 3-4-) and (ADH-3-5), but the appearance of these new isozymes was not associated with flooding tolerance. The relative activity of the slow moving isozymes 6, 7 and 8 was greatly reduced in both and the activity of band 2 was greatly increased in the extracts from both transgenics.

EXAMPLE 3

Expression of Alcohol Dehydrogenase in Callus Cultures

Callus was produced from petiole explants of each of the transgenic alfalfa plants and the nod-transgenic RA3 as described previously by Senaratna et al. (1989) on SH medium supplemented with 1 mg/L 2,4-D.

ADH had a broad pH activity range when assayed using ethanol as a substrate with an optimum at pH 8.5. ADH activity increased in the callus cultures of alfalfa with time reaching a maximum at 30 days. On average the transgenic plants had consistently higher rates of ADH activity than the non-transgenic control at all sampling times, but the differences were most pronounced at the later times. At day 30, the callus from all transgenic plants had higher activity and some transgenic callus had over 2.4 times the ADH activity of the nontransgenic control (Table 1).

TABLE 1

Expression of alcohol dehydrogenase activity (moles NADH produced per g protein) in alfalfa callus cultures at 15 and 30 days.

| Plant | Day 15 | | Day 30 | |
|---|---|---|---|---|
| | Activity | Std. Dev. | Activity | Std. Dev. |
| CONTROL | 4.10 | 0.57 | 7.80 | 0.88 |
| 2 | 4.05 | 0.31 | 10.67 | 0.80 |
| 3 | 4.60 | 0.42 | 18.03 | 1.80 |
| 4 | 4.33 | 0.032 | 18.00 | 2.65 |
| 5 | 4.70 | 0.75 | 18.93 | 3.41 |
| 6 | 3.88 | 0.67 | 10.40 | 3.26 |
| 7 | 4.63 | 0.45 | 14.00 | 0.44 |
| 8 | 4.98 | 0.60 | 9.27 | 1.00 |
| 10 | 4.70 | 0.10 | 12.13 | 2.58 |

Figure 4:
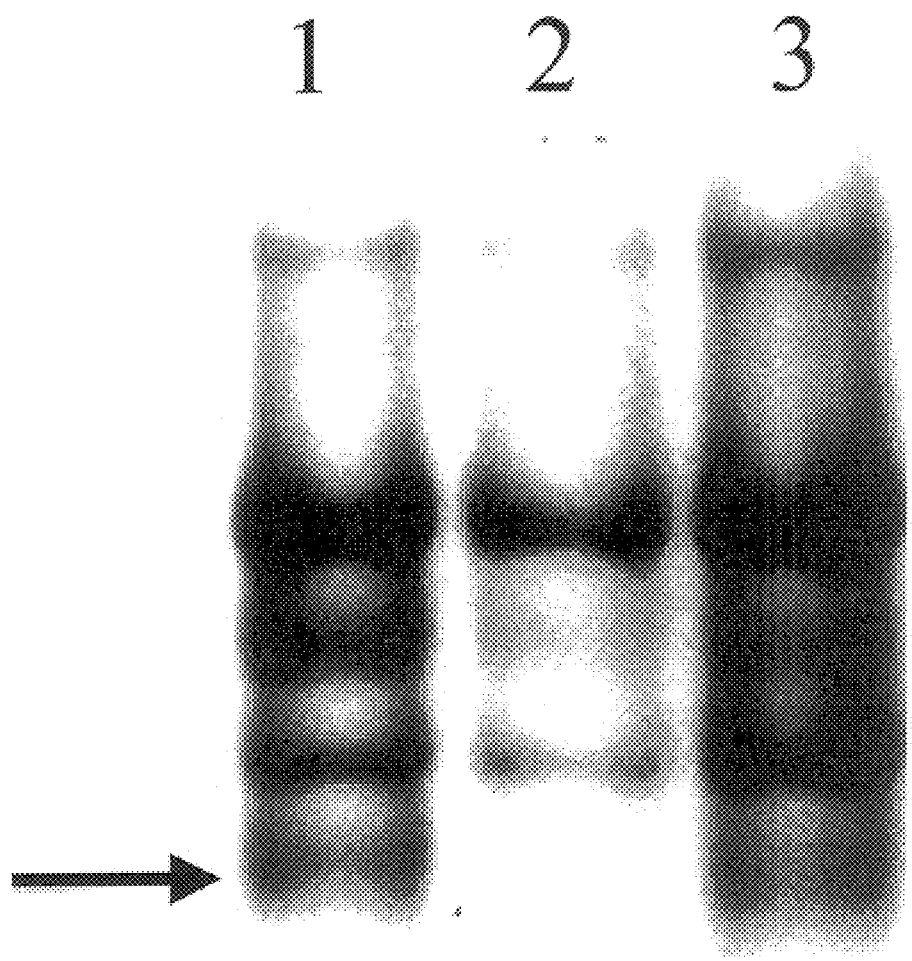
FIG. 4 shows native PAGE of alcohol dehydrogenase in callus cultures of control and transformed alfalfa. The arrow indicates the presence of an additional isozyme in the transgenic plants. Lane 2 is the control, RA3, and lanes 1 and 3 are two transgenic plants.

The callus contained at least four major ADH isoenzymes which could be resolved by native PAGE. There was a slow moving relatively faint band, a large, more intense band, which was actually composed of a family of isoenzymes, a third faint band, and a more intense fast moving band, which could also be resolved into several component isozymes if the native gel was run for longer periods of time (FIG. 4). The transgenic plants contained an additional ADH activity band which had a faster migration rate than any of the alfalfa ADH bands (arrow in FIG. 4). This band was present in all transgenic alfalfa samples and absent from all non-transgenic alfalfa samples.

EXAMPLE 4

Flooding Tolerance

Each of the transgenic plants and the original nontransgenic plant, RA3, were propagated by cuttings. The alfalfa plants were grown from cuttings with a 16 h photoperiod, PPFD of 250 $\mu$mol m$^{-2}$ s$^{-1}$, 22/17° C. (day/night) temperature. After approximately 6 weeks, the plants were defoliated, and grown for an additional 14 days to ensure uniform development and size. Plants were randomly divided between a non-stressed control and the flooding treatment. Preliminary experiments had shown a high degree of variability (experimental error) in assessing an alfalfa plant's response to flooding. Therefore, to minimize experimental variability, a split-plot in time arrangement with a systematic control was employed in this experiment. Within a block, vegetative propagules were arranged in 3×3 cells. The central cell was a propagule of the systematic control (untransformed RA3) and propagules of the 11 entries (10 transgenic and 1 control) were randomly assigned to all cells surrounding the systematic control. Two 3×3 cells comprised a block providing 16 entry cells per block. Since there were only 11 genotypes (entries), extra copies of the genotypes were randomly allocated to the remaining five cells in each block so that a similar number of propagules of each genotype were used over the entire experiment. This varied between 15 and 21 over the 3 repetitions of the experiment.

In the first and third repetitions, six blocks were used for the flooding stress and three blocks were used for the non-stress controls. The second repetition had four blocks for the flooding stress and three blocks for the non-stress control. The non-stressed control plants were grown in the same conditions as above. The flooding treatments were imposed in plastic trays which allowed the plants to be submersed to 2 cm above soil level, and were otherwise grown under the same conditions as the control plants for the 21 days of the flooding treatment. Prior to the flooding treatment the water was allowed to stand at room temperature for 7 days to equilibrate in temperature and oxygen content.

The plants were removed from the flooding treatment, defoliated and regrown for 3 weeks under the above growth conditions. The amount of shoot regrowth over this vegetative growth period is a measure of the quantity of carbohydrate and other root reserves, and the general vigor of the root system. Stressed plants or plants with a damaged root system would be expected to regrow slowly or not at all. The plants were defoliated, shoot dry matter weighed and the plants allowed to regrow for 2 more cycles of growth with harvesting at 3 week intervals. Dead plants were included in the calculations and assigned a regrowth value of 0.

Variance analyses and means were calculated using the general linear model procedure of the Statistical Analysis System, PC version (1988). Analyses were conducted within each stress level using a split plot in time arrangement with covariate (systematic control) model combined over repetitions. Genotypes and regrowths were assumed to be fixed effects. Means were compared to the untransformed control mean using a protected LSD test at p=0.05 (Steel and Torrie 1980). Significant (P<0.05) differences were detected among genotypes for both the non-stress and flooded stress treatments. No differences were detected between repetitions and interactions. In both the no-stress and flooding stress treatments, no significant (P>0.05) genotype x harvest effect was detected. This indicated that genotypes responded similarly over the three harvests and it was valid to compare genotype means when averaged over all harvests.

Under the non-stress treatment, the transformed genotypes were not significantly (P>0.05) different from the non-transformed RA3 control and averaged 292 mg/plant over the 3 harvests (data not shown). Significant differences were detected among transgenic plants because plant 1 was consistently stunted and had low shoot growth (108 mg/plant). The average shoot regrowth across all genotypes declined from the first to the third harvest because the 3 week interval is insufficient time to replenish root reserves for maximal regrowth. This effect was imposed intentionally to apply additional stress on the root reserves of the plants.

Following a 21 day flooding stress, shoot dry matter yield declined, on average to 78% of the non-stressed yield, averaging 64 mg/plant across all genotypes and harvests. The nontransgenic control plant had an average yield reduction of 80%. Among the transgenics, a diverse response to the stress was found—some appeared more sensitive, others more tolerant. Transgenics 2 (ADS-3-2) and 3 (ADH-3-3) were significantly (P<0.05) greater in regrowth yield compared to the untransformed control (Table 2). The regrowth of transgenic 3 (ADH-3-3) was more than double that of the non-transformed control after the flooding treatment.

TABLE 2

Shoot regrowth (mg/plant) after 21 days flooding over three cycles of regrowth

| Transgenic Plant | Regrowth (mg/plant) |
|---|---|
| CONTROL | 55 |
| 1 | 20 |
| 2 | 98* |
| 3 | 156* |
| 4 | 73 |
| 5 | 60 |
| 6 | 46 |
| 7 | 21 |
| 8 | 48 |
| 9 | 79 |
| 10 | 43 |

*Significantly (P < 0.05) different from the non-transformed control using a protected least-significant difference (LSD) means comparison.

The amount of shoot regrowth that occured after flooding stress is a measure of the general vigor of the root system and the quantity of carbohydrate and other root reserves.

EXAMPLE 5

Icing Tolerance

Transgenic and non-transgenic control plants were propagated by cuttings and grown as described above (Flooding Tolerance). The plants were arranged with a systematic control as before with the central cell of the 3×3 tray containing a non-transgenic control. The plants were grown for 6 weeks, defoliated, allowed to grow for 1 week and transferred to a low temperature acclimation chamber at constant 2° C., PPFD 250 $\mu$mol m$^{-2}$ s$^{-1}$, 12 h photoperiod for 4 weeks. This acclimation treatment induces the expression of ice-encasement tolerance as well as freezing tolerance. The plants were again defoliated and completely encased in ice at −5° C. in the dark for 10 days. The plants were then thawed and allowed to regrow under the standard growth conditions. Shoot dry matter was determined for three cycles of growth of three weeks duration each, as explained for flooding tolerance. Because of the low survival rate, the results were not statistically analyzed by analysis of variance, but standard deviations were calculated for the regrowth of each plant.

The ice-encasement stress was relatively severe and on average less than 50% of the plants of any genotype survived (Table 3). The non-transgenic control plant had only 19% survival and produced 5 mg/plant shoot regrowth. Two of the transgenic plants, 2 (ADH-3-2) and 3 (ADH-3-3), exhibited significantly higher survival and regrowth whereas the remainder were injured to a similar extent as the non-transgenic control.

TABLE 3

Shoot regrowth and plant survival of transgenic alfalfa plants after ice-encasement for 10 days.

| | Regrowth (mg/plant) | | |
|---|---|---|---|
| Transgenic Plant | Mean | Std. Dev. | Survival (%) |
| CONTROL | 5 | 12 | 19 |
| 2 | 26 | 66 | 33 |
| 3 | 32 | 79 | 50 |
| 4 | 5 | 17 | 7 |
| 5 | 9 | 19 | 18 |
| 6 | 1 | 2 | 10 |
| 7 | 0 | 0 | 0 |
| 8 | 1 | 2 | 18 |
| 9 | 0 | 0 | 0 |
| 10 | 6 | 14 | 33 | n = 12 for each transgenic and 16 for control

The amount of shoot regrowth that occured after freezing stress, as indicated in Example 1, is a measure of the general vigor of the root system and the quantity of carbohydrate and other root reserves.

EXAMPLE 6

Field Trials

A field trial of two primary transgenic plants (ADH-3-2 and ADH-3-3) was conducted at the Elora Research Station. The plots were established in the spring by transplanting rooted cuttings of each transgenic and control genotype. The test was arranged in a randomized complete block design with 4 replicates of 50 plants. Plot size was 1×1.5 m. Plants were harvested and dry matter herbage yields determined once in the year of transplanting, and twice for each of two subsequent years. Stand counts were taken in fall and the following two years in the spring to determine survival.

Figure 5B:
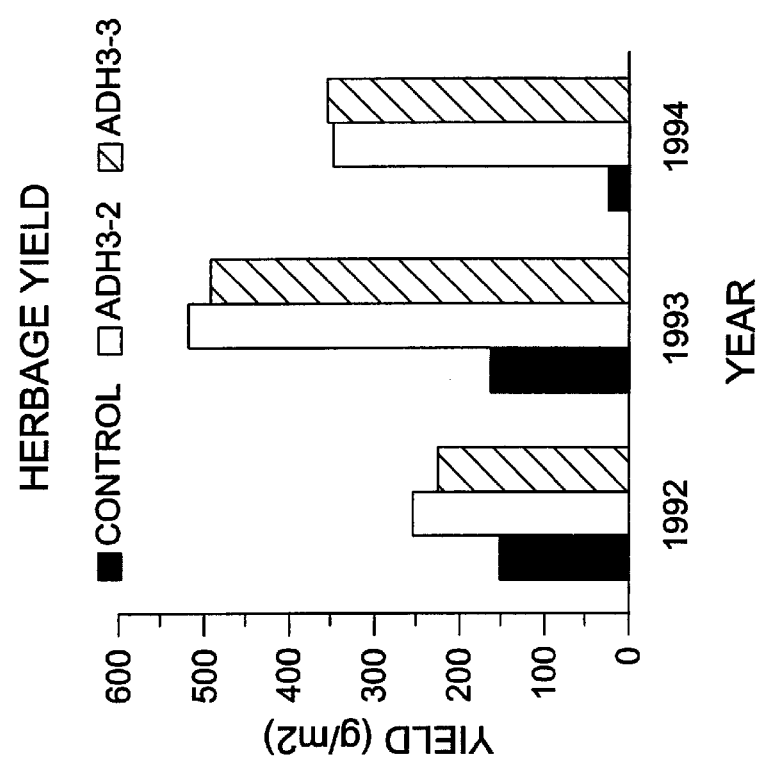
FIGS. 5A and 5B show winter survival and herbage yield in field trials at Elora Ontario of two alfalfa primary transgenic plants, ADH-3-2 and ADH-3-3, expressing alcohol dehydrogenase.
Figure 5A:
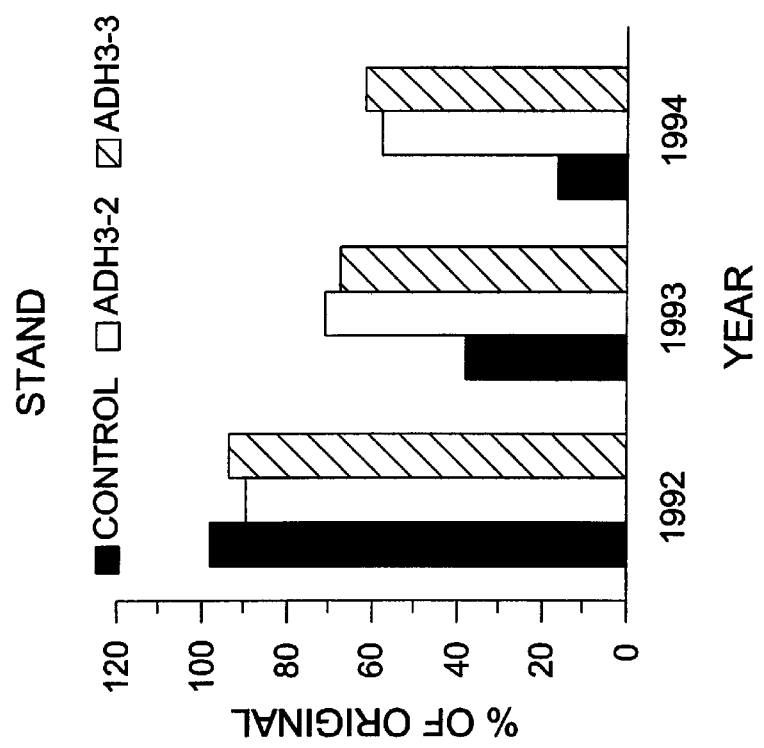

Over the three year period, the adh3 primary transgenics had greater forage yield and persistence compared to the control plants (FIG. 5).

In November, 25 random plants of each genotype were excavated and subjected to freezing stresses in an indoor freezing chamber. Plants were washed, acclimated at −2° in the dark for 24 hours and cooled at a rate of −2° C./h. Five random plants of each genotype were removed at −6, −8, −10 and −12° C. The plants were thawed overnight at 2° C. and potted and transferred to a greenhouse. Herbage yields were determined for each individual plant for two subsequent regrowth (28 day regrowth cycles). Average regrowth yields and $LT_{50}$ values (lethal temperature causing 50% death) were estimated for each genotype.

There were significant differences in plant survival for plants expressing the ADD transgene compared to the control non-transgenic genotype (Table 4). The plants with the ADH transgene had significantly higher regrowth yields. Both increased survival and increased herbage yield in the transgenic plants are a consequence of improved vigour of the root system and the quantity of carbohydrate and other root reserves.

TABLE 4

$LT_{50}$ estimates and regrowth yield over two harvests of alfalfa plants expressing an alcohol dehydrogenase transgene subjected to a laboratory freezing stress. Plants were field acclimated prior to exposure to freezing stress.

| Genotype | $LD_{50}$ | −6° C. | −8° C. | −10° C. | −12° C. |
|---|---|---|---|---|---|
| RA3 | −5.9 | 0.5 | 0.2 | 0 | 0 |
| RA3-ADH3-3 | −9.9 | 4.1 | 2.7 | 0.3 | 0 |
| RA3-ADH3-3 | −11.8 | 3.4 | 1.4 | 1.5 | 0.4 |
| se | | | | 1.20 | |

EXAMPLE 7

Inheritance of Transgenic Traits

The inheritance of phosphinothricin resistance was assessed in the transgenic plant ADH-3-3. This transgenic plant had higher ADH activity in extracts from aerobic roots (see FIG. 2) and was used as the paternal parent and another regenerating alfalfa genotype, C2-4, was the maternal parent.

The plants were cross pollinated by hand and seed collected and bulked for analysis. Sixty seven plants were grown from the seed under conditions as described above. A representative leaf from each plant was streaked with 100 mg/L phosphinothricin. The leases were visually assessed for injury on a scale of 1 to 5, with 5 being severe burning and necrosis. The treatments were repeated twice over time. Ratings of 1 or 2 were considered tolerant, ratings of 3 to 5 were susceptible, and plants with variable responses between the two tests were considered susceptible. Since the majority of readings were either 1, 4, or 5, the distinction between tolerance and susceptibility was usually obvious. In terms of resistance to phosphinothricin, 35 plants were tolerant, 32 were susceptible (23+9 variable), indicating an inheritance ratio of 1:1.

EXAMPLE 8

Inheritance of Transgene $T_1$ Generation

The inheritance of phorphinothricin resistance was assessed suing the transgenic plant RA3-ADH3-3. The transgenic was used as the paternal parent and a non-transgenic regenerating alfalfa genotype, C2-4, 4 from the University of Guelph alfalfa embryogenesis breeding program was used as the maternal patent. The alfali plants were grown with a 16 h photoperiod, PPFD of 250 $\mu$mol m$^{-2}$s$^{-1}$, 22/17° C. (day/night) temperature. The plants were cross pollinated by hand and $F_1$ seed collected and bulked for analysis. Sixty seven $F_1$ plants were grown from the seed and a representative leaf from each plant was streaked with 100 mg/L phosphinothricin. The leaves were visually assessed for injury on a scale of 1 to 5, with 5 being severe burning and necrosis. The treatments were repeated twice over time. Ratings of 1 or 2 were considered tolerant, ratings of 3 to 5 were susceptible, and plants with variable responses between the two tests were considered susceptible. Since the majority of readings were higher 1, 4, or 5, the distinction between tolerance and susceptibility was usually obvious. In terms of resistance to phosphinothricin, 35 plants were tolerant, 32 were susceptible (23+9 variable). This ratio did not differ from a 1:1 ratio (Yate's $\chi^2$=0.06, P=0.8070) expected for a single transgene insertion.

Backcross Breeding Program

Two $F_1$ genotypes, Bast-50 and Bast-61, were selected from the cross C2-4×RA3-ADH-3-3 based on expression of bar and adh3. These two $F_1$ genotypes were used to initiate three backcross populations involving University of Guelph non-transgenic breeding materials and produce the following backcross (BC,) populations:

BC-A: crosses to six N3 plants selected for low self-seed set from the University of Guelph embryogenic breeding population ('92);

BC-B; crosses to 10 plants selected from the University of Guelph high persistence and seed yield;

BC-C: crosses to 12 plants selected from a population which combined the branched root character with multileaf-higher forage quality.

For each BC1 family, 18–72 plants were screened for the herbicide marker, and the best plants from each family selected for a subsequent set of crosses. To produce $BC_2$ populations:

$BC_2$, BC-A: selected BC1 progenies of BC-A were crossed to selected plants from University of Guelph population '92 with high yield & persistence.

$BC_2$, BC-B. selected BC1 progenies were crossed to selected plants from University of Guelph population A29 (Syn-1) with high yield & persistence.

$BC_2$, BC-C: selected BC1 progenies were crossed to another group of plants selected for combined branched root and multileaf attributes.

In the spring, seedlings of each $BC_2$ family were grown in the greenhouse, sprayed with phosphinothricin (Ignite) at 5 wks age, and all survivors planted at the Elora research station following protocols authorized by Plant Products Division, Agriculture and Agri-Food Canada. Plants were defoliated at the end of June to determine dry matter herbage yields. Within each population, the best families for herbage yield and persistence were identified and the best plants within each selected family were identified during the regrowth period.

Vegetative propagules of selected plants were obtained and returned to the University of Guelph transgenic containment facility. These plants were used to initiate a half-sib family recurrent selection program in 1998. The selected $BC_2$ plants were intercrossed by hand in the greenhouse and half-sib progeny, 24 plants per family, were planted in flats in the winter. At 5 weeks of age the seedlings were sprayed with the herbicide Liberty at an application rate of 0.6 kg ai/ha as described previously. The follwoing spring, surviving half-sib progeny were transplanted to a nursery in May at the Elora research station following protocols authorized by Plant Products Division, Agriculture and Agri-Food Canada (test 98-UoG 1-075-AL01-288-ON01-01). Plants were defoliated twice that season.

Test Cross of $BC_1$ Generation

Figure 6A:
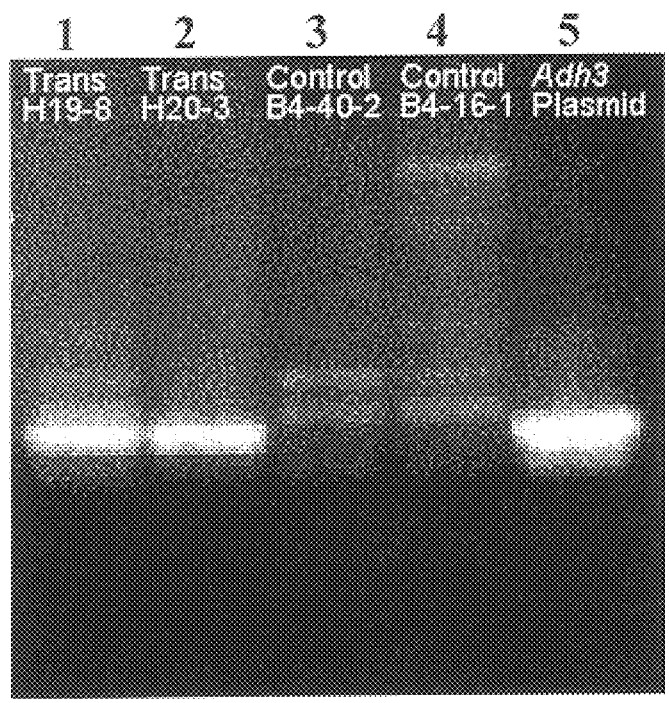
FIGS. 6A and 6B show Polymerase Chain Reaction (PCR) products formed in the analysis of the transgenic *Medicago sativa* plants containing pADH3.
Figure 6B:
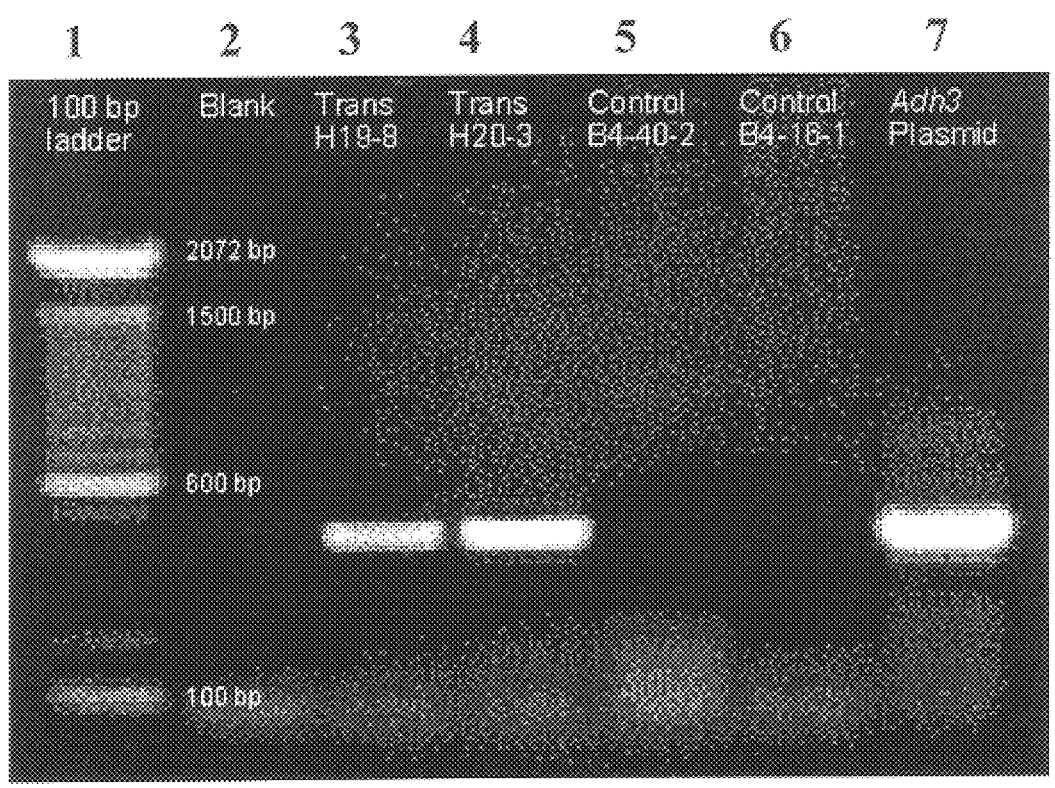

Paired reciprocal crosses were made between $BC_1$ transgenic plants (H19, H20-3) and two unrelated non-transgenic plants (B4 16-1, B4 40-2) using hand emasculation by suction. Genotypes B4 16-1 and B4 40-2 were non-transgenic plants possessing a multileaf, branched root, to unifoliate phenotype. Approximately 60 $F_1$ progeny for each cross were evaluated by PCT for the presence or absence of the Adh3/Bar transgene. DNA was extracted with 400 mL homogenizing buffer (250 mM NaCl, 25 mM EDTA, 0.5% SDS, 200 mM tris-HCl, pH 7.4). For the PCR reaction, 25 ng of DNA was combined with 1.5 ml of 15 mM MgC 12, 1 unit taq polymerase, 2.5 ml 10×buffer, 2.5 ml dNTP and 2 ml of each primer made to a final volume of 25 ml with water. One primer pair were used for an internal region of the bar gene (41 1 bp product) and a second pair were used for an internal region of the adh3 gene (558 bp product). PCR products were visualized on a 0.8% agarose gel with ethidium bromide (FIG. 6).

Figure 7:
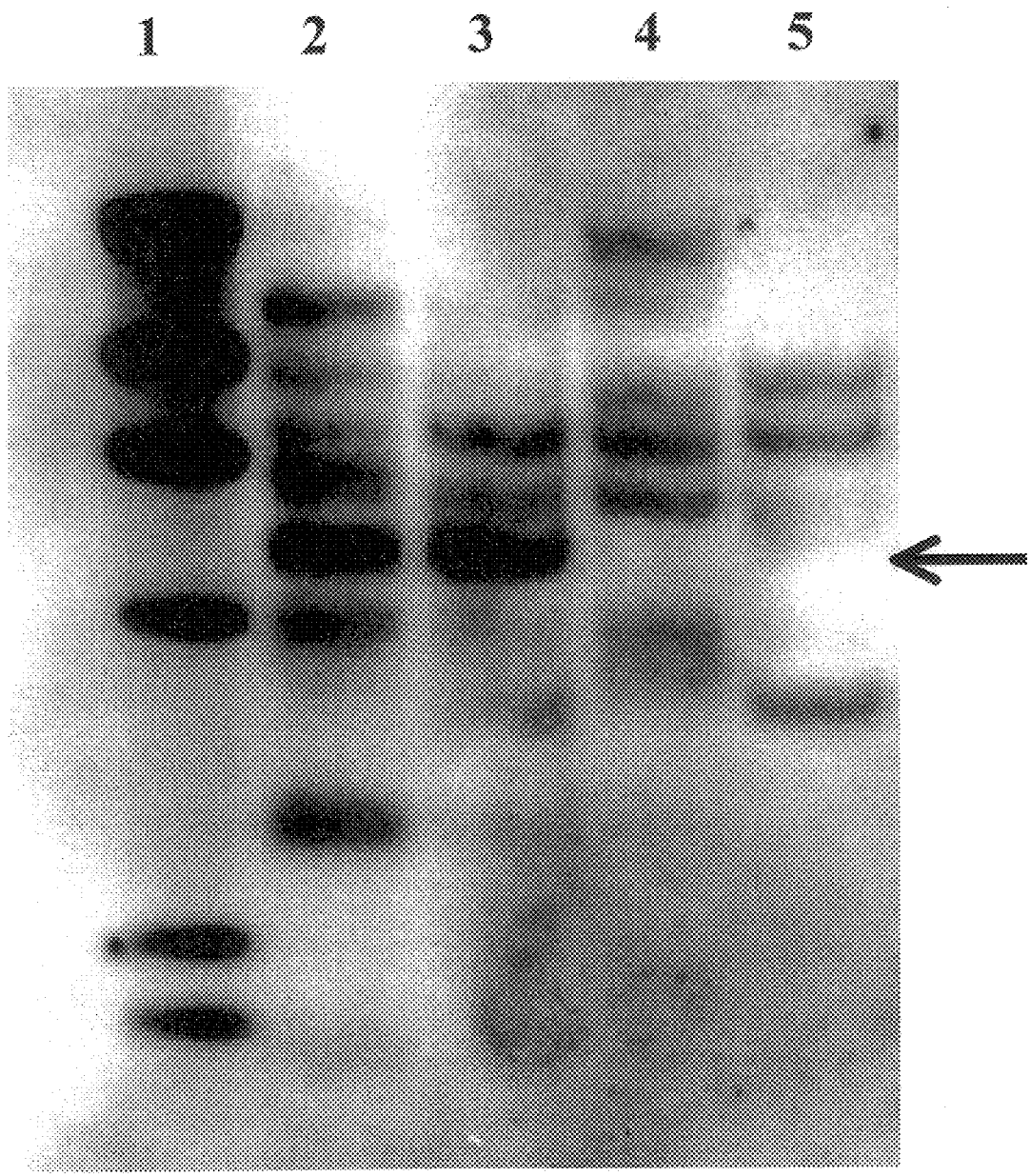
FIG. 7 shows Southern analysis for adh transgene from pADH3 in plants of *Medicago sativa*. Lane 1 (left) is marker lane; lanes 2 and 3 represent independent transgenic plants, lanes 4 and 5 are non-transgenic control plants. The arrow indicates the unique transgene bands. The adh probe used hybridizes to both the adh transgene and the adh native genes. The bands that are unique to each plant represent the transgenes; the bands that are common to the plants represent the native adh gene family.
Figure 8:
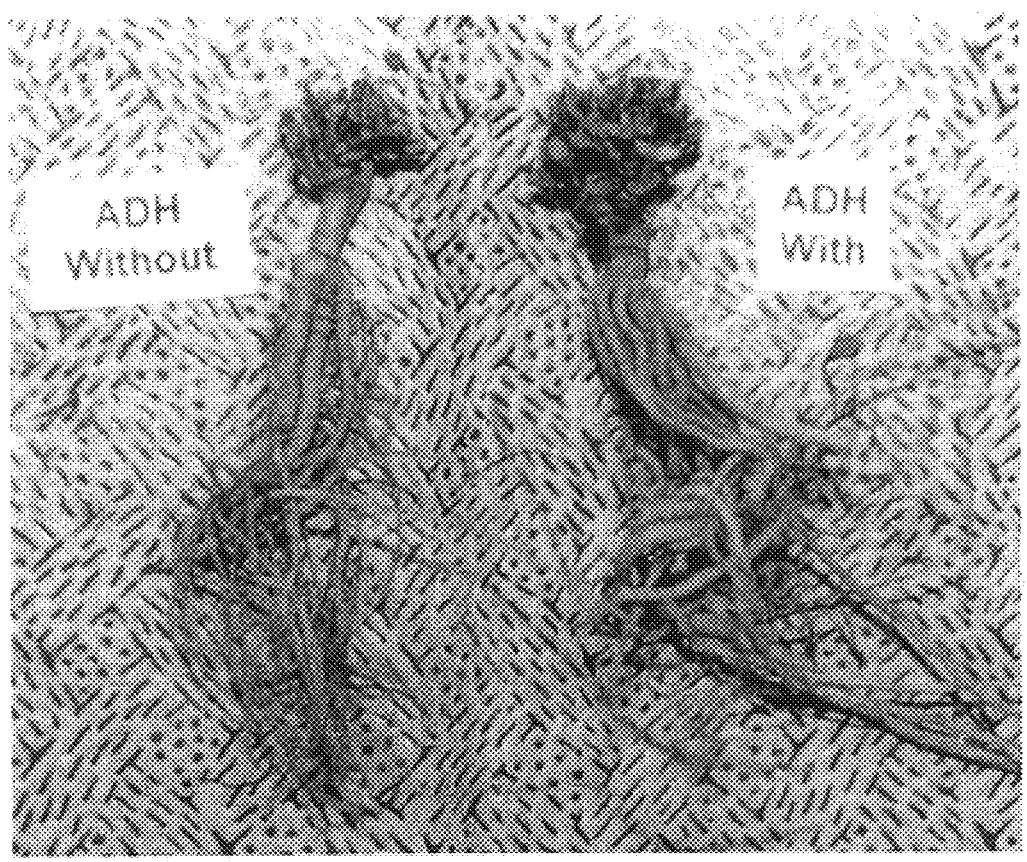
FIG. 8 shows a photograph of the crown and roots of two sibling *Medicago sativa* plants—one containing the ADH transgene, the other not containing the ADH transgene. Note the dramatic difference in size of the root.

DNA was extracted for Southern hybridization according to Dellaporta et at (1983). Plasmid DNA preparations were prepared using the Promega Whizard mini-prep kit and diluted in water to a final concentration of 100–125 ng/lll. Purified DNA was treated with the restriction enzymes at 5–10 fold excess. All samples were separated using a 0.8% agarose gel. After electrophoresis the gel was blotted overnight onto positively charged nylon membrane as outlined in Assubel et al. (199)). After blotting, the membranes were cross-linked using W light. Subsequent Southern analysis was based on the Boehringer Mannheim (BM) Digoxigenin chemiluminescent system (van Miltenburg et al, 1995). Analysis of the transgenic plants confirmed that there were 1 or 2 full insertions of the T-DNA in the chromosomes of each of the transgenic plants. Two fragments (~6264 and ~5385 bp) of the Adh3/Bar transgene insert were observed in plant H19-8 and only one fragment (~5385 bp) in plant H20-3 (FIG. 7).

A series of F1 crosses were performed between three selected $BC_2$ plants, as female parents, and a series of other plants not carrying the bar-adh transgene. Crosses were performed by hand without pollen control. $F_1$ progeny were grown in a greenhouse and classified using PCR as described earlier. The results are presented in Table 5. For most crosses, the observed segregation ratio followed the 1:1 ratio expected for a single-locus transgene insertion.

TABLE 5

Observed segregation ratios and chi-square goodness of fit tests for the $F_1$ test-cross progeny of $BC_2$ alfalfa plants carryig the bar-adh transgene. The expected ratio for a single transgene insertion was 1:1 (with:without)

| Test-cross | | Observed number | | | |
|---|---|---|---|---|---|
| Female | Cross | With bar-adh | Without bar-adh | Yate's$\chi^2$ | P |
| 92-109-P2 | C38 | 35 | 28 | 0.57 | 0.4497 |
| 92-112-P1 | C48 | 40 | 50 | 0.90 | 0.3428 |
| 92-120-P1 | C39 | 32 | 31 | 0.00 | 1.000 |
| | C47 | 34 | 62 | 7.59 | 0.0059 |

Experimental Varieties

A population of $BC_2$ plants were divided into two subpopulations, with- and without-the Bar/ADH transgene, using PCR analysis as described earlier. These $BC_2$ plants were used as parents to create two experimental synthetic varieties, one with the gene (24-parent synthetic) and one without the gene (25-parent synthetic). Hand pollinations were performed to produce the Syn-1 generation seed of the two synthetic varieties in the fall and winter. Crosses were performed by hand as well as using leafcutter bees (*Megachile rotundata*) as pollinators.

In the fall, 11 plants were selected from within the half-sib progeny field test established in the following spring. Plants were selected based on their tolerance to Liberty, visual herbage yield and vigour, and freedom from potato leafhopper feeding injury. Three vegetative propagules of each selected plant were returned to the greenhouse and intercrossed by hand and by leafcutter bees (*Megachile rotundata*) to produce the Syn-1 generation in during winter.

Syn-1 Generation

Seed of the Syn-1 generation of the experimental variety derived from selected $BC_2$ plants carrying the transgene was used for this study. Four sets of 96 Syn-1 generation progeny were planted in a greenhouse and scored using PCT using primers for the ADH transgene as described earlier. The expected segregation ratio in the Syn-1 generation was 3:1 (with:without the transgene). The observed number in each class and the result of the Yate's corrected chi-square test is presented in Table 6. The goodness-of-fit test indicated that the observed ratio followed that expected for a 3:1 segregation ratio. In accordance with previous types of progeny tested, the transgene segregated as a single-gene insertion.

TABLE 6

Observed segregation ratios and chi-square goodness of fit tests for the Syn-1 progeny of $BC_2$ alfalfa plants carrying the bar-adh transgene. The expected ratio for a single transgene insertion was 3:1 (with:without).

| | Observed Number | | | |
|---|---|---|---|---|
| Group | With bar-adh | Without bar-adh | Yate's$\chi^2$ | P |
| 1 | 65 | 26 | 0.44 | 0.5056 |
| 2 | 67 | 22 | 0.01 | 0.9512 |
| 3 | 69 | 20 | 0.18 | 0.6684 |
| 4 | 55 | 31 | 5.02 | 0.00250 |
| | | | $\chi^2$ | |
| Pooled | 256 | 99 | 1.58 | 0.2090 |

EXAMPLE 9

Field Trial

Two subpopulations, one comprising Bar/ADH transgene, the other without, were vegetatively propagated and transplanted to the field in the spring for evaluation of performance in competitive plantings. The field trial was conducted at the Elora Research Station following protocols authorized by Plant Products Division, Agriculture and Agri-Food Canada. Replicated plots were established by transplanting rooted cuttings of each transgenic and control genotype in 1×2 meter rectangular plots at 100 plants per plot. Plants were harvested twice in the year of transplanting on 1 July and 2 September.

Root Growth

Samples were dug from the field on 14 April. Fresh and dry weights of crowns and taproots were determined, the latter after drying for two weeks at 70° C. Plants that contained the ADH transgene had larger roots than those that did not have the ADS transgene (FIG. 5 and Table 7).

TABLE 7

Increased size of roots and crowns from two sibling *Medicago sativa* populations - one containing the ADH transgene, the other not containing the ADH transgene.

| Vector | Crown | Root |
|---|---|---|
| Fresh Weight (g) | | |
| With ADH | 1.53 | 3.84 |
| Without ADH | 1.11 | 1.86 |
| LSD (0.05) | NS | 1.50 |
| Dry Weight (g) | | |
| With ADH | 0.41 | 0.93 |
| Without ADH | 0.32 | 0.56 |
| LSD (0.05) | NS | 0.34 |

LSD(0.05) is the Least Significant Difference between means at the 5% level of probability; n=5, NS—not significantly different Herbage yield of the alfalfa plots transplanted under oats was measured at Elora. Seasonal herbage yields were significantly higher for plants carrying the ADH transgene compared to plants not carrying the transgene (Table 8). There was an average 24% difference in seasonal herbage yields between the two subpopulations.

TABLE 8

Herbage yield of alfalfa expressing an alcohol dehydrogenase transgene at Elora in 1998. Alfalfa plants were transplanted in 1997 under oats and three forage harvests taken in 1998.

| Entry | Harvest 1 | Seasonal Total |
|---|---|---|
| Without ADH | 311 | 501 |
| With ADH | 363 | 617 |
| std error | 22.5 | 35.1 |

A second test was established at Elora with alfalfa planted as pure stands. This experiment was harvested for forage yield on a three-cut management. The persistence of plants carrying the ADH transgene was greater than those not carrying the transgene when grown in pure stand (Table 9).

TABLE 9

Herbage yield of alfalfa expressing an alcohol dehydrogenase transgene grown in pure stand and in binary mixtures with timothy. Test established 1997 and herbage yields measured 1998, Elora, Ontario.

| | Herbage yield (g/m$^2$) | | Percent survival |
|---|---|---|---|
| Entry | Harvest 1 | Total | 60 |
| Without ADH | 194 | 417 | 60 |
| With ADH | 242 | 545 | 72 |
| se | 28.7 | 45.4 | 5.9 |

In addition, the seasonal herbage yields were higher for plants carrying the ADH transgene. Te yield enhancement was on the order of 30%. In mixture with timothy, there was no difference detected between the two groups presumably because of the growth compensation ability of the timothy plants. Plant survival was no different between the two groups when grown in mixture with timothy. This indicated that plants carrying the transgene did not negatively affect the growth of timothy.

EXAMPLE 10

Dig Field Trial

From January to March, cuttings were made of the two populations one with and the other without ADH. The trial was established with 2 replications at Elora, Ontario in May and 2 replications at New Liskead in June. The plots were established with rooted propagules of the same transgenic plant per row, 11 different transgenic plants per plot (other transgenic plants were included in this trial but the data are not shown) and 24 plots per replication. One plot was dug on each sampling date from June to October to measure root (including crown) and shoot dry weight. The plants were defoliated twice at Elora and twice at New Liskeard prior to flowering; these periods correspond to the first and second growth cycles (Tables 10 and 11, respectively). Statistical analysis was conducted as a split-plot factorial experiment of location×plant×date. At both locations, there was no difference in the growth of the shoots between the two populations (Tables 10 and 11). However, the roots of the population with the ADH transgene were larger than those without the transgene. This effect was apparent throughout the growing season although the difference was larger later in the season (Table 11).

TABLE 10

Shoot and root (including crown) dry weights (g/plant) of two alfalfa populations, with and without the ADH transgene, sampled at Elora and New Liskeard (NL) during the first growth cycle after transplanting.

| | Shoot | | Root | |
|---|---|---|---|---|
| | Elora | NL | Elora | NL |
| Without ADH | 2.4 | 1.1 | 0.4 | 0.3 |
| With ADH | 2.3 | 1.1 | 0.6 | 0.4 |
| std error | 0.20 | 0.31 | 0.05 | 0.11 |

TABLE 11

Shoot and root (including crown) dry weights (g/plant) of two alfalfa populations, with and without the ADH transgene, sampled at Elora and New Liskeard (NL) during the second growth cycle after transplanting

| | Shoot | | Root | |
|---|---|---|---|---|
| | Elora | NL | Elora | NL |
| Without ADH | 3.4 | 3.0 | 1.8 | 2.2 |
| With ADH | 3.1 | 3.2 | 2.0 | 2.8 |
| std error | 0.18 | 0.31 | 0.15 | 0.39 |

In the following spring, the larger root system the previous year caused differences in the rate of shoot regrowth and consequently, those plants with the ADH transgene had greater shoot and root dry weights (Table 12).

TABLE 12

Shoot and root (including crown) dry weights (g/plant) to two alfalfa populations, with and without the ADH transgene, sampled at Elora and New Liskeard (NL) during the second growth cycle after transplanting.

| | Shoot | | Root | |
|---|---|---|---|---|
| | Elora | NL | Elora | NL |
| Without ADH | 3.85 | 2.55 | 2.15 | 3.23 |
| With ADH | 7.52 | 3.98 | 3.61 | 4.11 |
| std error | 0.93 | 0.93 | 0.45 | 0.45 |

EXAMPLE 11

Increased Root Development and Storage Organ (Stolon) Size in Grasses and Legumes Altering the sink strength of stolons and roots in grasses and legumes is accomplished by introducing an ADH transgene into desired plants. In greenhouse trials, creeping bentgrass (*Agrostis palustris*) and white clover (*Trifolium repens L.*) plants with and without an ADH transgene are propagated. Control plants of the same clone are included. Growth and development of plants are measured at weekly intervals over a number of regrowth cycles by sampling plants and separating them into leaves, stolons and roots, for determination of weight.

EXAMPLE 12

Preparation of Medicago Sativa Transformed with SOD

The enzyme superoxide dismutase (SOD; EC 1.15.1.1) is a metalloprotein which catalyzes the dismutation of superoxide to hydrogen peroxide and molecular oxygen (Scandalios, 1993; Bowler et al., 1992; Bowler et al., 1994). This is the initial step in the Asada-Halliwell pathway that has been well characterized in chloroplasts. In plants, it can take three forms: Cu/Zn—, Mn— and Fe-SOD, which are primarily targeted to the chloroplast, mitochondria and cytosol, respectively, and it has long been deemed an essential component of the oxidative detoxification pathway.

Figure 13:
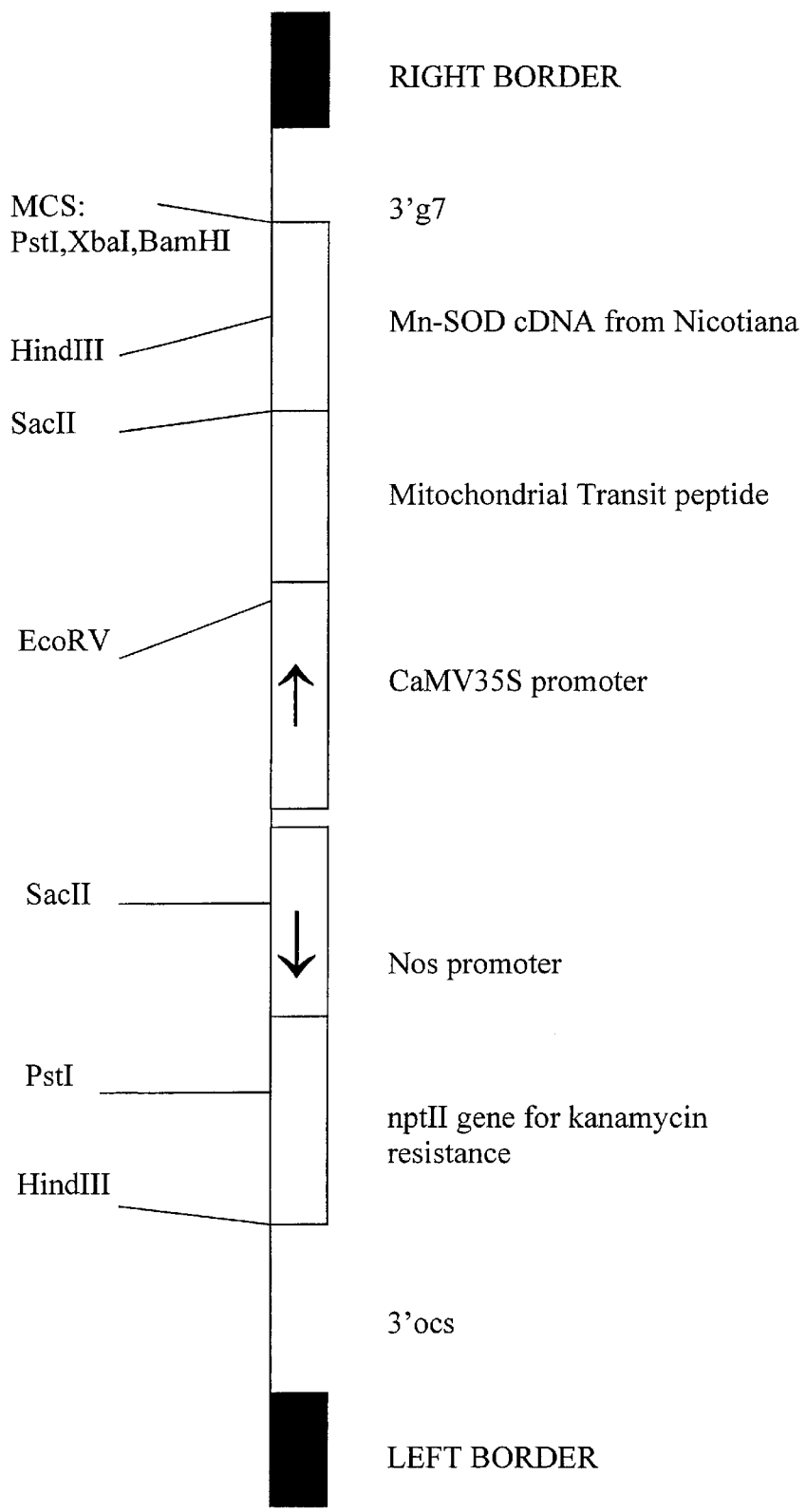
FIG. 13 shows a restriction map of the T-DNA region in pMitSOD vector used to transform Medicago sativa. The T-DNA has the Mn-SOD cDNA that encodes a peptide with a transit peptide targeting the protein to the mitochondria.
Figure 14:
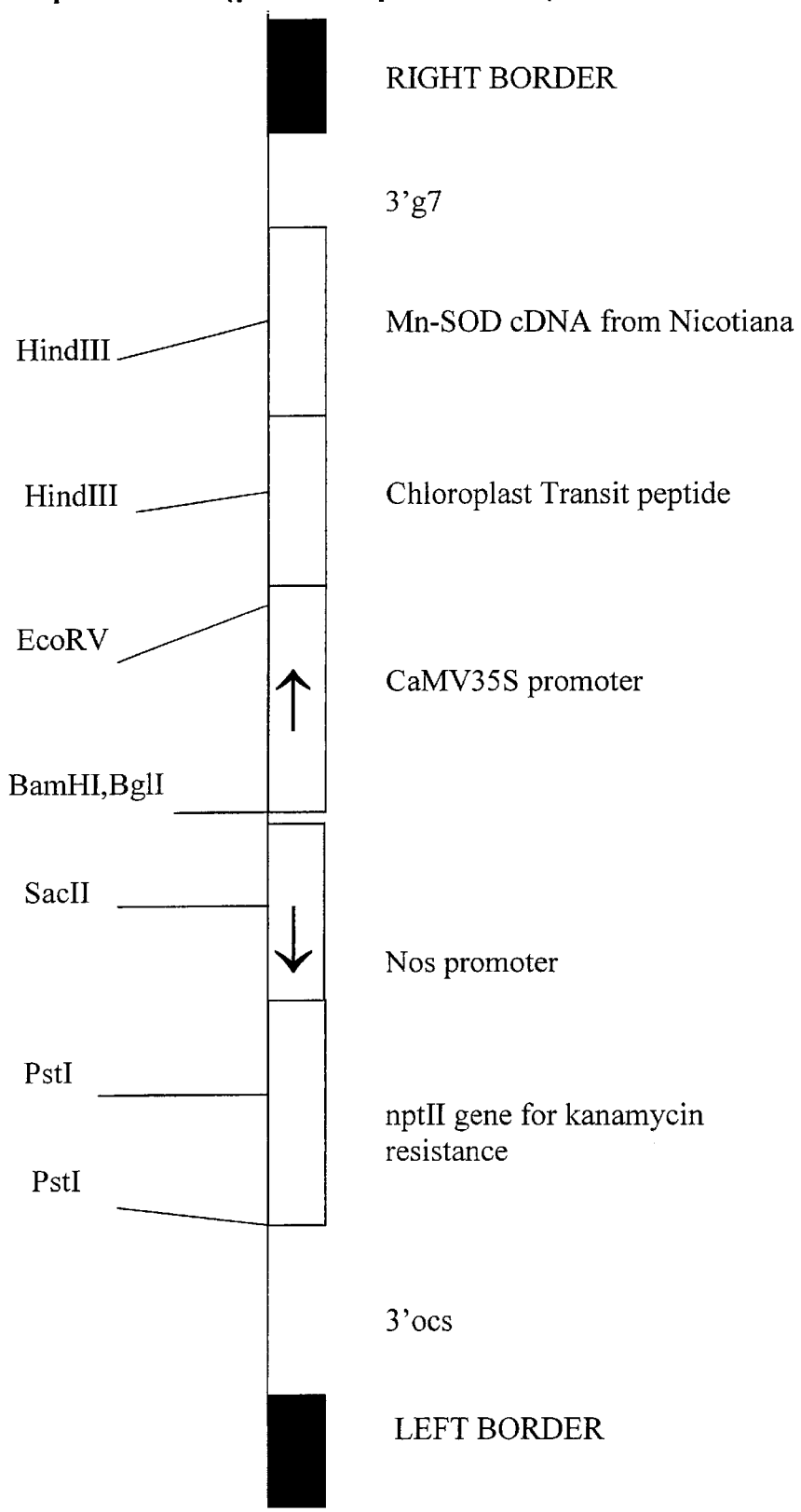
FIG. 14 shows a restriction map of the T-DNA region in pChlSOD vector used to transform Medicago sativa. The T-DNA has the Mn-SOD cDNA that encodes a peptide with a transit peptide targeting the protein to the chloroplast.
Figure 15:
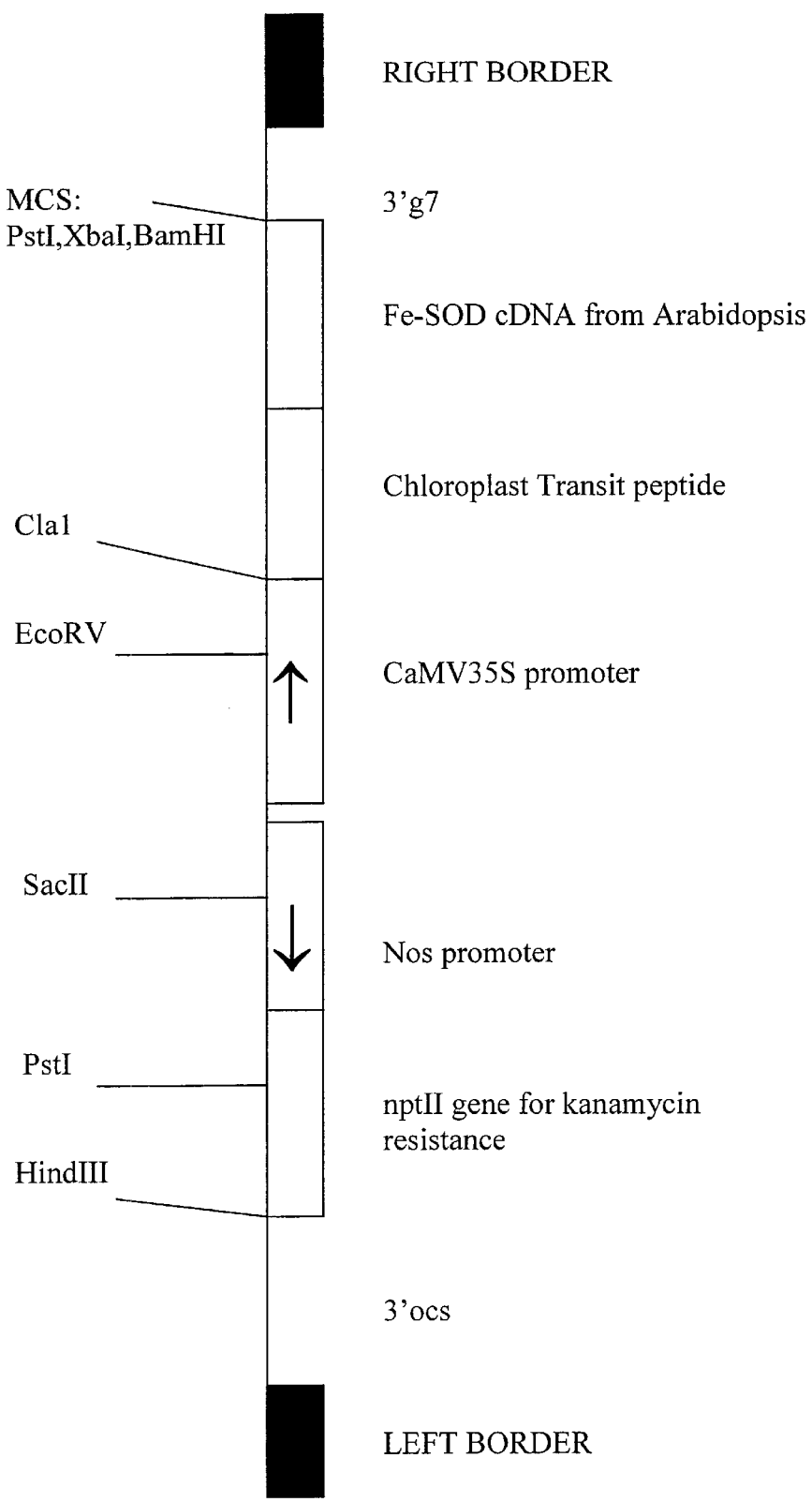
FIG. 15 shows a restriction map of the T-DNA region in pFeSOD vector used to transform Medicago sativa. The T-DNA has the Fe-SOD cDNA that encodes a peptide with a transit peptide targeting the protein to the chloroplast.

Transformation Vectors pMitSOD (PSOD1) is a binary vector with the NPT II gene under control of the NOS promoter and the Mn-SOD gene under control of the 35S promoter. Details of vector construction are given by Bowler et al. (1991). The MnSOD cDNA is from *Nicotiana plumbaginifolia* (GenBank Accession X14482). NPT II, coding for neomycin phosphotransferase, was obtained from *E. coli*. The NOS promoter is from the Nopalie synthase gene from wild-type Agrobacterium and the 35S promoter is from the Cauliflower mosaic virus (CaMV). The pMitSOD construct has a transit peptide leader sequence which targets the gene product to the mitochondria. The respective genes are followed by fragments encoding termination and polyadenylation signals of octopine synthase (3'OCS) and T-DNA gene 7 (3'g7), both from Agrobacterium. Details are shown in FIG. 13.

pChlSOD (pSOD4) is a binary vector with the NPT II gene under control of the NOS promoter and the Mn-SOD gene under control of the 35-S promoter. Details of vector construction are given by Bowler et al. (1991). The MnSOD cDNA is the same as pMit SOD. The pChlSOD construct has a transit peptide leader sequence which targets the gene product to the chloroplast (GeneBank Accession A09029). The respective genes are followed by fragments encoding termination and polyadenylation signals of octopine synthase (3'OCS) and T-DNA gene 7 (3'g7), both from Agrobacterium. Details are shown in FIG. 14.

pSOD10 (pFeSOD) is a binary vector with the NPT II gene under control of the NOS promoter and the Fe-SOD gene under control of the 35S promoter. Details of vector construction given by Van Camp, et al. (1996). The Fe-SOD cDNA was obtained from Arabidopsis (GenBank Accession M55910) and other details are as described above. The Fe-SOD cDNA from Arabidopsis has a transit peptide leader sequence, which was retained, which targets the gene product to the chloroplast. Details are shown in FIG. 15.

Plant Transformation and Screening

Four different clones of alfalfa, designated N4-4-2, V4-11-3, S4-15 and S4-16, were selected from the University of Guelph plant breeding program. Petiole explants of *Medicago sativa* were co-cultivated with an overnight culture of Agrobacterium tumefaciens C58C1 Rif pMP90 containing the binary vectors pMitSOD, pChlSOD or pSOD10. The explants were co-cultivated on SH induction medium (Shetty and McKersie, 1993) containing 288 mg/L proline, 53 mg/L thioproline, 4.35 g/L K2SO4 and 100 µM acetosyringinone for 3 days in the dark. The explants were washed in half-strength MS medium (Murashige and Skoog, 1962) and plated on the same SH induction medium without acetosyringinone but containing 500 mg/L claforan and 50 mg/L kanamycin. After several weeks, somatic embryos were transferred to BOi2Y development medium (Bingham et al, 1975) containing no growth regulators, no antibiotics and 50 g/L sucrose. Somatic embryos were subsequently germinated on half-strength MS medium. Rooted seedlings were transplanted into pots containing Turface (Plant Products, Mississauga, Ontario) in a greenhouse at approximately 23° C./18° C. (day/night) and a minimum 16-h photoperiod.

PCR Screening

Figure 16:
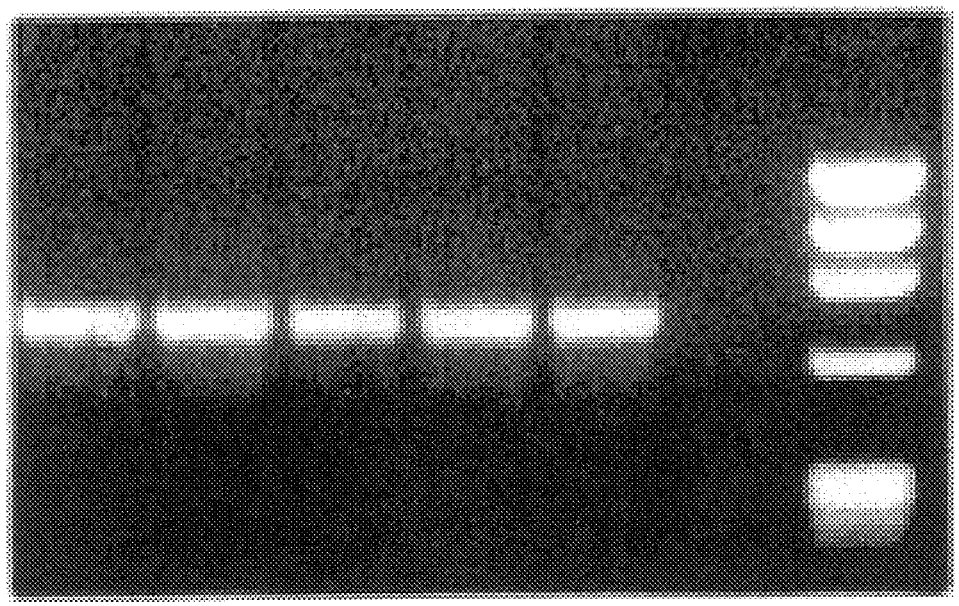
FIG. 16 shows PCR detection of nos-nptII transgene from pMitSOD and pChlSOD in individual transgenic plants of Medicago sativa. Lanes 1 to 5 are different independent transgenic plants; lane 6 is a non-trans genic control; lane 7 contains markers.

Prior to transfer to the greenhouse, the putatively transgenic plants were screened for the presence of the nos-nptII transgene using PCR. DNA was extracted with 400 µl homogenizing buffer (250 mM NaCl, 25 mM EDTA, 0.5% SDS, 200 mM tris-HCl, pH 7.4). The supernatant of a 13,000×g ecentrifugation was mixed with 300 µl isopropanol. DNA was collected at the interface, washed and resuspended in water. The quality and concentration of the DNA was confirmed using a 0.8% agarose gel with ethidium bromide staining. For the PCR reaction, 25 ng of DNA was combined with 1.5 µl of 15 mM MgC12, 1 unit taq polymerase, 2.5 µl 10×buffer, 2.5 µl dNTP and 2 ml of each primer made to a final volume of 25 µl with water. The primers used were 5' AGCTGTGCTCGACGTTGTCAG-3' (SEQ ID NO:2) and 5' GGTGGGCGAAGAACTCCAGCA-3' (SEQ ID NO:3). The PCR program was 5 min at 94° C., then 25 cycles of 94° C. for 15 sec., 65° C. for 30 sec., and 72° C. for 60 sec., followed by 5 min at 72° C. and holding at 4° C. PCR products were visualized on a 0.8% agarose gel with ethidium bromide (FIG. 16).

Approximately 90% of the regenerated plants scored positive in this screen. Only PCR positive plants were transferred to the greenhouse for further study.

Southern Hybridization

Purified DNA from alfalfa was treated with the restriction enzymes EcoRV and EcoRI at 5–10 fold excess. All samples were separated using a 0.8% agarose gel. After electrophoresis the gel was blotted overnight onto positively charged nylon membrane as outlined in Ausubel et at. (1991). After blotting the membranes were UV cross-linked. Subsequent Southern analysis was based on the Boehringer Mannheim digoxigenin chemiluminescent system (van Miltenburg et al., 1995). The DIG-labeled DNA hybridization probes were synthesized by using the "Expand" enzyme to enzymatically label PCR products with DIG-dUTP as described by Boehringer Mannheim (PCR DIG Probe Synthesis Kit). Probes were synthesized for both the kanamycin and the mitochondrial SOD genes using 200 pg purified plasmid DNA as the template. The PCR primers for synthesis of the kanamycin probe were 1 µM each of 5'-AGCTGTGCTCGACG-TTGTCAC-3' (SEQ ID NO:4) and 5'-GGTGGG-CGAAGAACTCCAGCA-3' (SEQ ID NO:3). Annealing temperature was 65° C. and the product size was 732 bp. The primers for the SOD gene were 5'-GAGCAGA- CGGACCTTAGC-3' (SEQ ID NO:5) and 5'-AGAAA-CCAAAGGGTCCTG-3' (SEQ ID NO:6); with a 55° C. annealing temperature and a 511 bp product.

Figure 17:
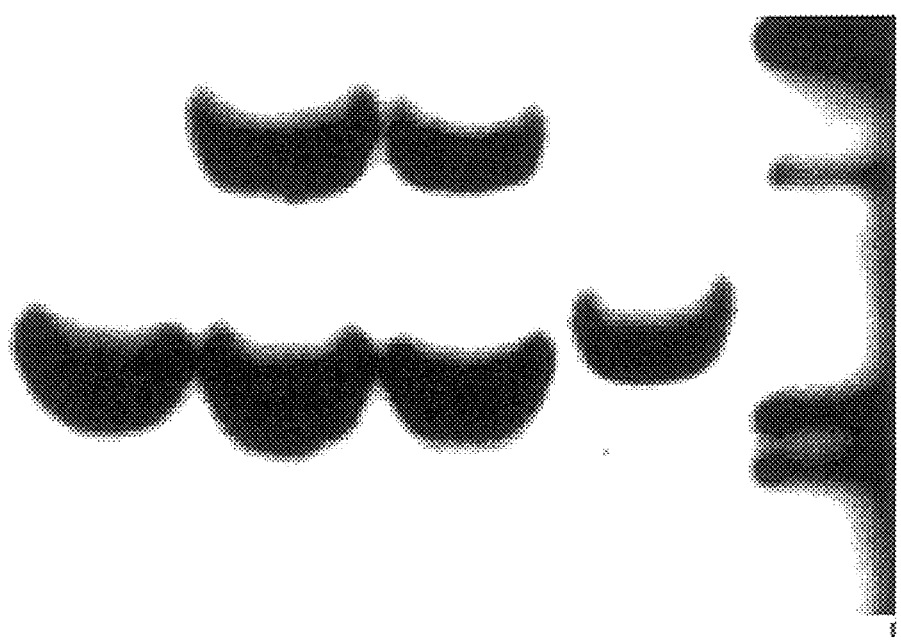
FIG. 17 shows Southern analysis for nos-nptII transgene from pMitSOD in four individual transgenic plants of Medicago sativa (labelled as 3, 4, 5 and 6).

Southern analysis of eight transgenic plants confirmed that there were 1 or 2 full insertions of the T-DNA in the chromosomes of each of the transgenic plants. Not all transgenic plants were tested (FIG. 17).

Superoxide Dismutase Activity

SOD was extracted from 2–3 fully expanded leaf blades (or other tissue as indicated) from a vegetative stage shoot. The sample was frozen in liquid nitrogen, ground and resuspended in 150 ml of 50 mM KH2PO4, pH 7.8. The homogenate was centrifuged at 13,000×g for 15 min and the protein content of the supernatant was determined (Bradford, 1976). A constant volume (20 $\mu$l) was applied to a 13% polyacrylamide gel with a 4% stacking gel (McKersie et al., 1993). One lane of each gel contained 0.5 units of bovine Cu/Zn-SOD (Sigma Chemical) as an internal standard. The gel was stained with nitroblue tetrazolium and riboflavin (Sigma Chemical) at 4° C., then developed on a light box for 20 min. Areas of superoxide dismutase activity were negatively stained against a blue background.

An image of the gel was captured using a CCD video camera and Northern Exposure Software (Empix Imaging, Mississauga, Ontario). The area under each SOD isozyme peak was calculated using Microsoft Excel. The data were expressed as a percentage of total activity by calculating area of isozyme peak/total area of all SOD peaks×100%. Alternatively, the data were expressed as units of SOD activity per g protein, calculated as area of individual peak/area of internal standard×concentration of internal standard.

Figure 18:
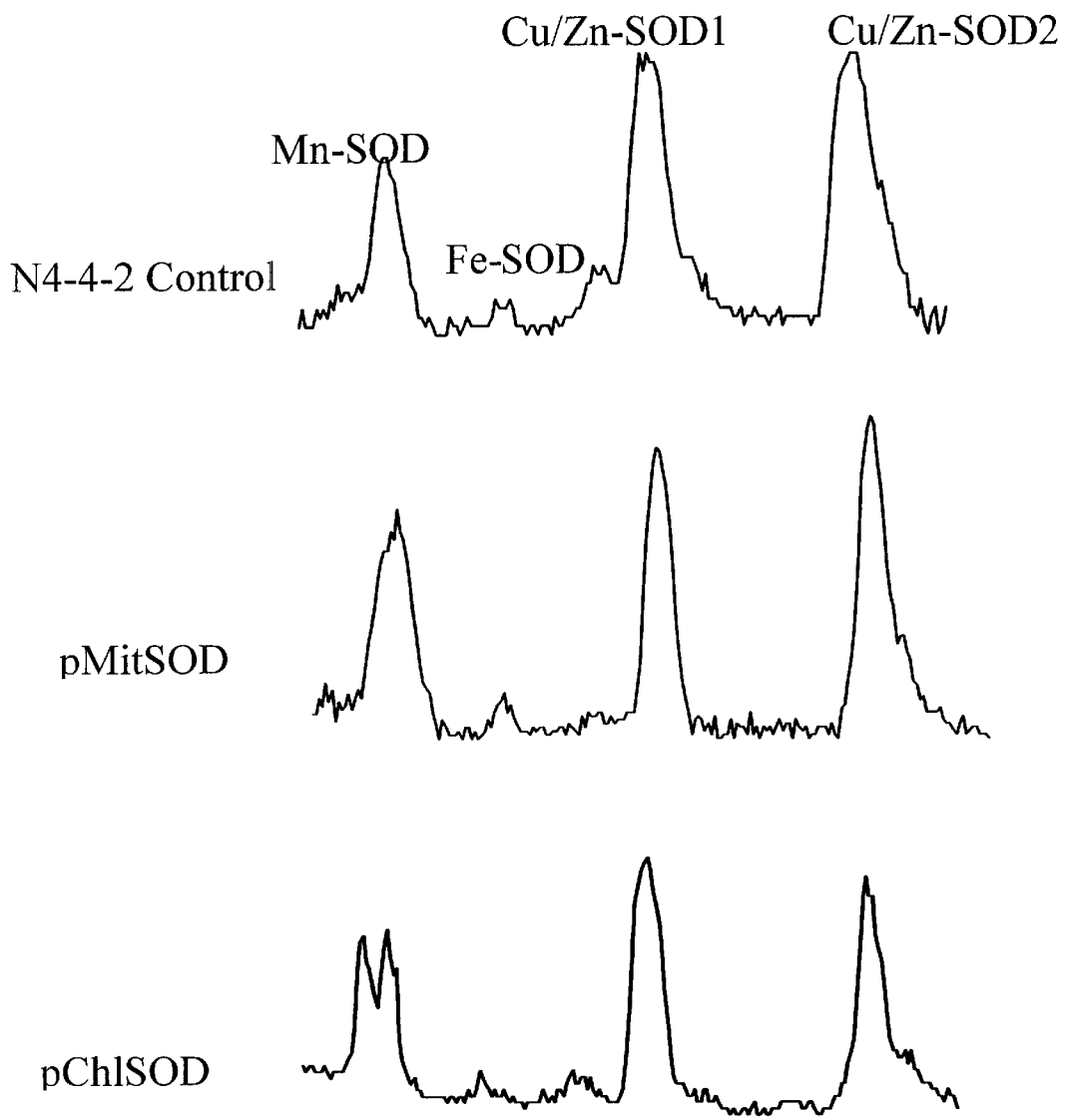
FIG. 18 shows scans of native PAGE gels showing SOD activity in leaf extracts of independent transgenic Medicago sativa plants expressing pMitSOD or pChlSOD compared to control N4. Note the presence of a relative increase in the area of the Mn-SOD in the pMitSOD transgenic and the presence of a new Mn-SOD band in the pChlSOD transgenic.

The non-transgenic control N4 plant had three major SOD bands—a fast moving chloroplastic form of Cu/Zn-SOD, a slower moving cytoslic form of Cu/Zn-SOD and a mitochondrial Mn-SOD (FIG. 18). A small Fe-SOD peak was occasionally detected between the Mn-SOD and cytosolic Cu/Zn-SOD, but its activity was quite labile and not included in the calculations of total SOD activity. The transgenic plants had an additional Mn-SOD enzyme superimposed on the native Mn-SOD isozyme in the native gels. In the case of the pMitSOD, the two Mn-SOD forms were not resolved by PAGE, but in the case of the pChlSOD, two distinct Mn-SOD bands were apparent. The difference in the mobility of the mitochondrial and chloroplast targeted forms of Mn-SOD possibly reflects differences in the cleavage site of the transit peptide, or another post-transcriptional modification. The amount of each SOD isozyme was quantified in two ways. The area of each peak from the linescan was calculated and expressed relative to the total area of SOD activity in each lane to determine its proportion of total SOD activity. This method compensated for differences in the amount of the extract applied to the gel and for differences in the staining intensity among gels. However, the method assumed that Cu/Zn-SOD was not affected by expression of the Mn-SOD transgene. So in some experiments, the amount of each SOD isozyme was quantified by expressing its area relative to the area of an internal standard (bovine Cu/Zn-SOD) on the same gel to calculate specific activity (units g-1 protein). The amount of bovine Cu/Zn-SOD applied was linearly related to the area of the peak over the range used in these experiments (data not shown).

Based on native PAGE analysis, Mu-SOD activity was increased by a variable amount among the independent transgenic plants containing either pMitSOD or pChlSOD. In about 25% of the transgenic plants from either transformation vector, Mn-SOD activity was reduced or not changed. In the majority of the transgenic plants, Mn-SOD activity was increased less than two-fold. In only a small proportion of the transgenic plants, Mn-SOD activity was doubled relative to total SOD activity, Field Trial A field trial was conducted at the Elora Research Station following protocols authorised by Plant Products Division, Agriculture and Agri-Food Canada (tests 97-UOG1-075-ALF02-177-ONO1-01; -ALF03-236-ONO1; -ALF04-224-ONO1-01). Four replicated plots of 1×1.5 m rectangular plots were established in May by transplanting 100 rooted propagules of each transgenic per plot. Each plot consisted of a population of independent transgenic plants for each construct. Plants in the direct seeding trial were harvested twice in the year of transplanting on 1 July and 2 September.

Root Growth

In November samples were dug from the field trial. Fresh and dry weights of crowns and taproots were determined, the latter after it was dried for two weeks at 70° C. A second set of samples was dug from the same plots in April the follwoing year. In November samples, the root and crown systems were larger in all the transgenic plants than in the controls (Table 13).

TABLE 13

Increased size of roots and crowns of transgenic *Medicago sativa* plants expressing different superoxide dismutase transgenes. Plants were dug in November and the following April.

| | November | | April | |
|---|---|---|---|---|
| Vector | Crown | Root | Crown | Root |
| Fresh Weight (g/plant) | | | | |
| Control | 1.16 | 3.67 | 0.69 | 2.56 |
| MitSOD | 1.52 | 7.09 | 3.27 | 8.96 |
| ChlSOD | 1.08 | 4.76 | 0.75 | 2.65 |
| FeSOD | 1.35 | 5.40 | 0.81 | 2.38 |
| LSD (0.05) | 0.31 | 1.42 | 1.50 | 1.50 |
| Dry Weight (g/plant) | | | | |
| Control | 0.30 | 1.31 | 0.21 | 0.79 |
| MitSOD | 0.44 | 2.62 | 1.03 | 2.64 |
| ChlSOD | 0.29 | 1.77 | 0.22 | 0.84 |
| FeSOD | 0.38 | 1.93 | 0.24 | 0.73 |
| LSD (0.05) | 0.10 | 0.53 | 0.44 | 0.44 |

Figure 19:
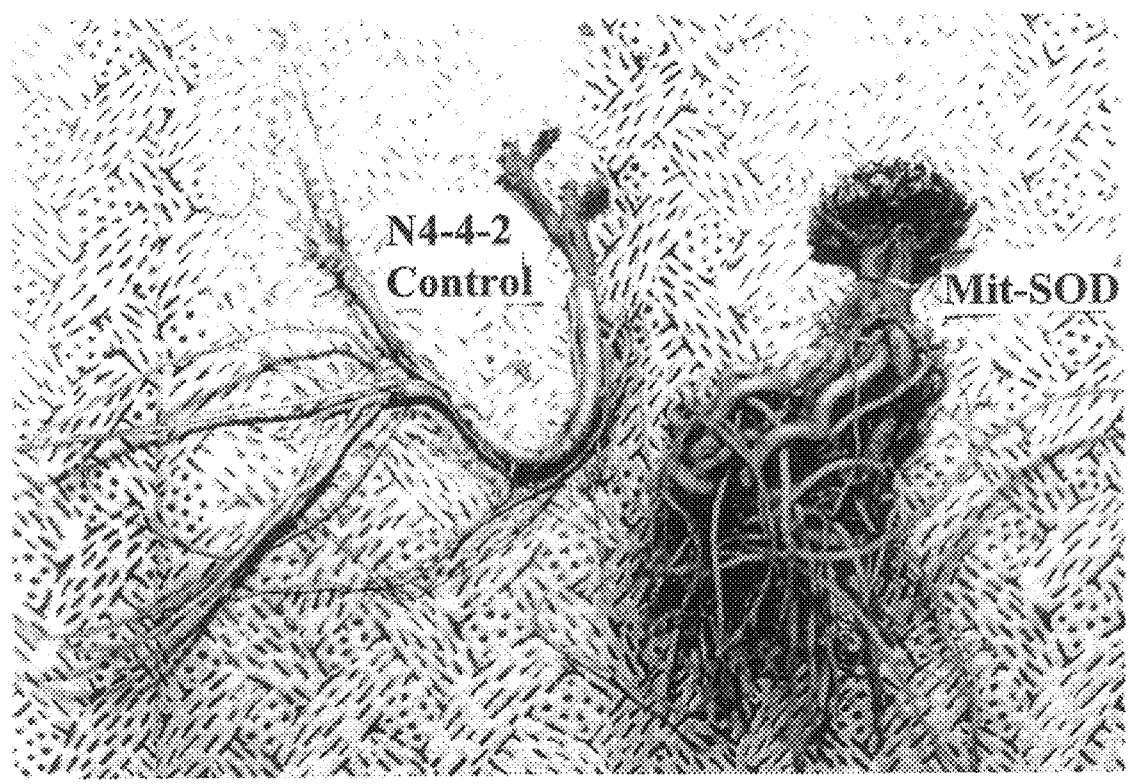
FIG. 19 shows plant samples of alfalfa roots dug in April from a field trial (see Example 12).
Figure 20:
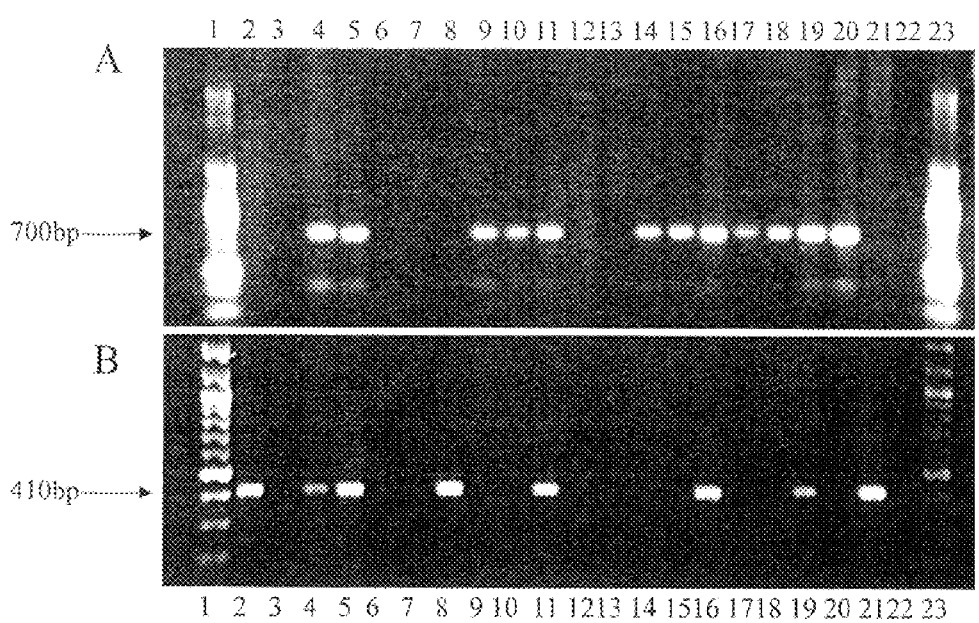
FIGS. 20A and 20B show PCR analysis of dual transgenics containing SOD and ADH transgenes.

LSD (0.05) is the Least Significant Difference between means at the 5% level of probability; n = 15 for fall; n = 5 for spring The roots and crowns of the plants containing the T-DNA from pMitSOD had greater fresh and dry weight than the other plants (FIG. 19). Those that contained the T-DNA from pChlSOD and pFe-SOD were slightly larger than the control but smaller than those with pMitSOD Note that both pChlSOD and pFe-SOD produced a SOD enzyme that was targeted to the chloroplast.

The roots and crowns of the plants containing the T-DNA from pMitSOD did not have a greater proportion of their dry matter associated with protein or carbohydrate reserves (data not presented). On a dry weight basis the root and crown of all SOD transgenic plants contained the same amount of glucose, fructose, raffinose, starch and protein as the control. Therefore, the total available quantity of reserves available to support the growth of a new shoot from the crown is considerably greater in the transgenic plants due their larger mass.

Dig Field Trial: Root Growth

From January to March cuttings were made of the primary transgenic plants. Because of the large numbers of plants required to establish the field trial, some transgenic plants were bulked together and randomly propagated. A similar procedure was used for control N4-4-2 plants. Other transgenic plants were included in this trial but the data are not shown.

Permits to conduct the field trails were obtained from Canadian Food Inspection Agency (98-UOG1-075-ALF #-ONO1-01 for trials at Elora and 98-UOG1-075-ALF #-ON30-01 for trials at New Liskeard where # is 03-177 for MitSOD, 04-083 for ChlSOD and 02-224 for FeSOD). The trial was established with 2 replications at Elora, Ontario on May, and at 2 replications at New Liskeard on June. The plots were established with 5 rooted propagules of the same transgenic plant per row, 11 different transgenic plants per plot and 24 plots pet replication. One plot was dug on each sampling date from June to October 1998 to measure root, crown and shoot dry weight. The plants were defoliated twice at Elora and once at New Liskeard prior to flowering.

Statistical analysis was conducted as a split-plot factorial experiment of location×plant * date. The main effects and most interactions were statistically significant at the 5% level of probability. The plantilocation interaction is shown in Table for the three tissues and total dry weight. ChlSOD-J48 had larger roots, shoots and crowns averaged over all sampling times than N4 control plants. The effect was greater at New Liskeard than Elora (Table 14).

TABLE 14

Shoot and Root (includes crown) dry weights( g/plant) of transgenic alfalfa expressing SOD transgenes sampled at Elora and New Liskeard from June to October. Values are averaged over 2 reps of 15 samples at Elora and of 11 samples at New Liskeard.

| Location | Plant | N | Root | Shoot | Total |
|---|---|---|---|---|---|
| Elora | N4 control | 30 | 1.41 | 2.59 | 4.00 |
| | MitSOD-J4 | 29 | 1.39 | 2.62 | 4.02 |
| | ChlSOD-J48 | 30 | 1.87 | 3.21 | 5.08 |
| | FeSOD-J13 | 30 | 1.28 | 2.42 | 3.69 |
| Location | Mean | 119 | 1.49 | 2.71 | 4.20 |
| NL | N4 control | 21 | 1.54 | 2.11 | 3.65 |
| | MitSOD-J4 | 24 | 1.64 | 2.37 | 4.01 |
| | ChlSOD-J48 | 22 | 2.36 | 2.81 | 5.17 |
| | FeSOD-J13 | 18 | 2.15 | 2.47 | 4.62 |
| Location | Mean | 85 | 1.91 | 2.44 | 4.35 |

LSD at 5% are 0.58 (shoot) and 0.47 (root).

EXAMPLE 13

Figure 9:
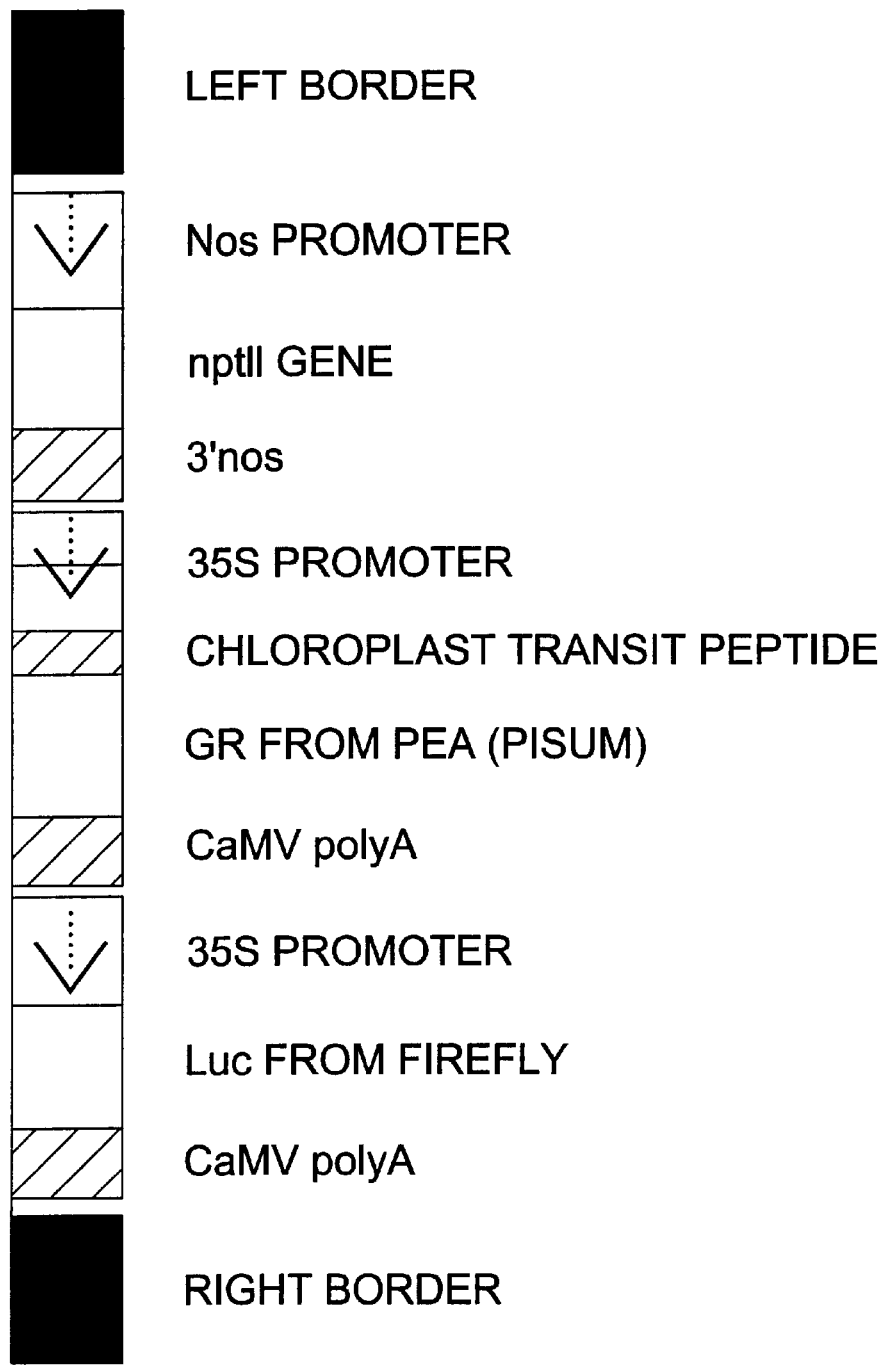
FIG. 9 is a map of the T-DNA region in pGR36 vector used to transform *Medicago sativa*. The T-DNA has the glutathione reductase gene that encodes a peptide with a transit peptide targeting the protein to the chloroplast.
Figure 10:
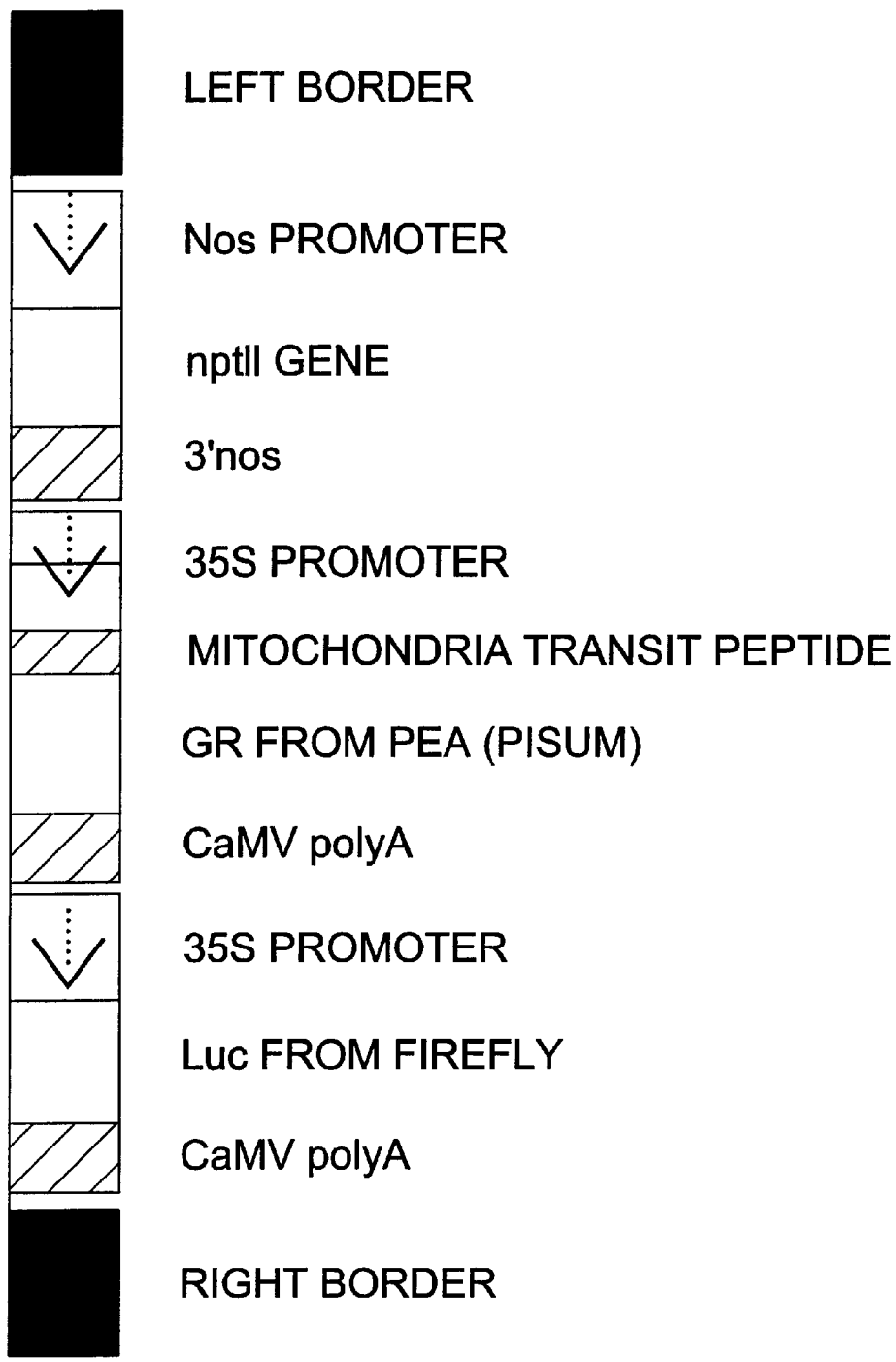
FIG. 10 is a map of the T-DNA region in pGR40 vector used to transform *Medicago sativa*. The T-DNA has the glutathione reductase gene that encodes a peptide with a transit peptide targeting the protein to the mitochondria.
Figure 11:
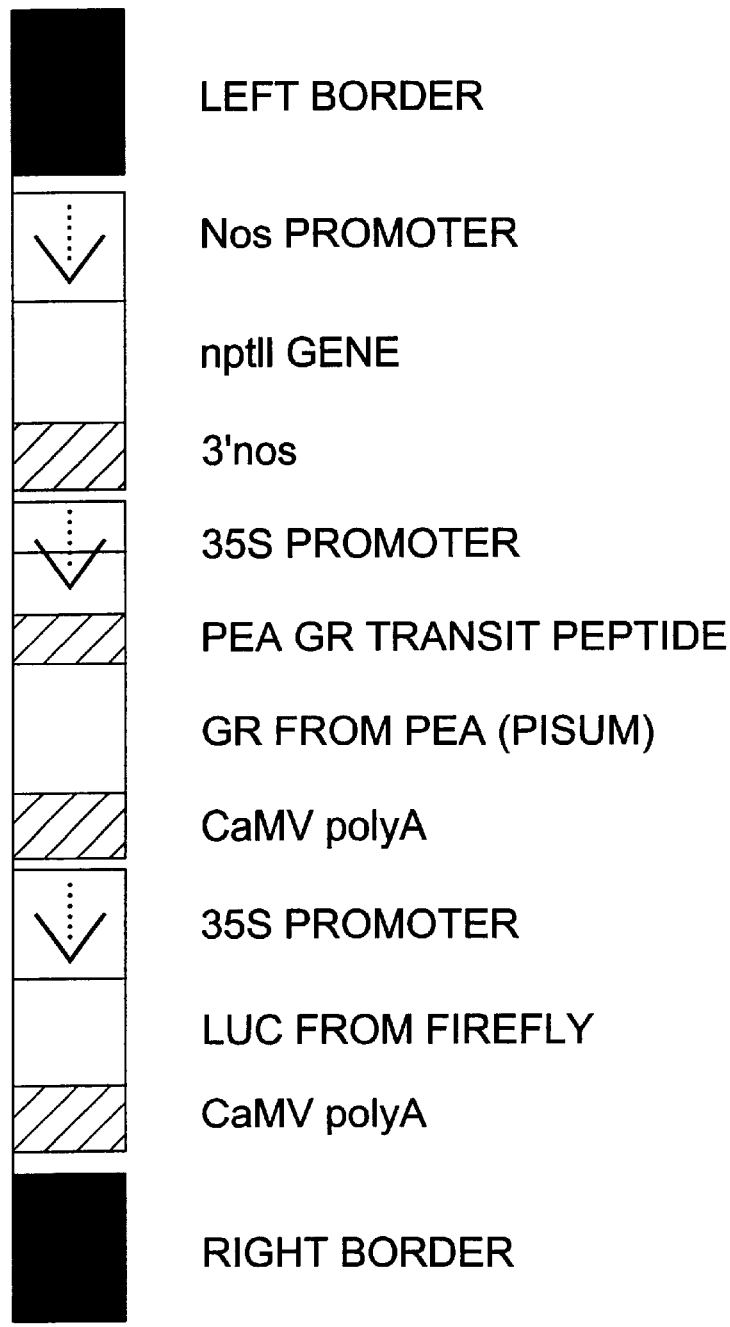
FIG. 11 is a map of the T-DNA region in pGR46 vector used to transform *Medicago sativa*. The T-DNA has the glutathione reductase gene that encodes a peptide with a transit peptide targeting the protein to the chloroplast and to the mitochondria.
Figure 12:
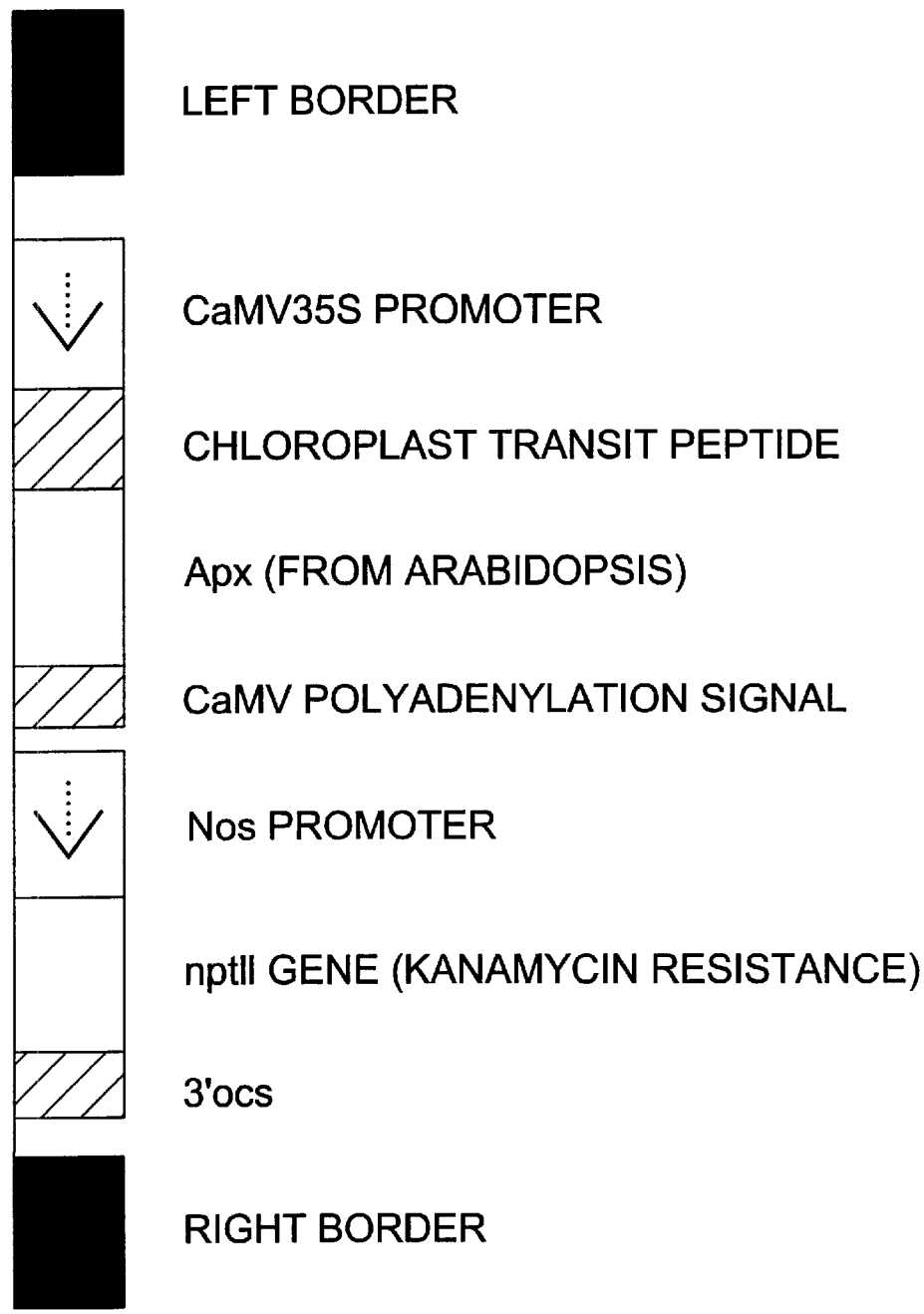
FIG. 12 is a map of the T-DNA region in pAPX vector used to transform *Medicago sativa*. The T-DNA has the ascorbate peroxidase cDNA that encodes a peptide with a transit peptide targeting the protein to the chloroplast.

Transgenic Plants Expressing Super Oxide Dismutase, Ascorbate Peroxidase and Glutathione Reductase Have Greater Root Growth The expression of other transgenes may also alter the redox potential of root cells, change the sink strength of roots and increases the mass of the roots. A field trial was conducted using tooted cuttings made from alfalfa plants transformed (as per Example 1) with glutathione reductase transgene targeted to the chloroplast (FIG. 9), mitochondria (FIG. 10), or both (FIG. 11), or with an ascorbate peroxidase transgene (FIG. 12). Control plants of the same clone, but without the transgenes are included as a control.

The rooted cuttings are transplanted to the field. Samples of each plant are taken at two week intervals from June until December and divided into leaves, stems, crown and root, and weighed. The field plots are grown under normal alfalfa management and are defoliated at the late bud stage of development. The field trial was established and sampled as described in Example 10, (Elora only).

As indicated in Table 15, the transformed plants had larger root mass.

TABLE 15

Root (including crown) dry weights (g/plant) of primary trangenic alfalfa sampled at Elora during the first and second growth cycles after transplanting and in the spring of the following year.

| | First cycle | Second cycle | spring |
|---|---|---|---|
| Control, non-transgenic | 0.65 | 1.92 | 2.54 |
| superoxide dismutase | 0.92 | 2.50 | 3.64 |
| glutathione reductase | 0.68 | 2.00 | 2.98 |
| ascorbate peroxidase | 0.78 | 2.05 | 3.58 |
| std error | 0.06 | 0.16 | 0.25 |

All vectors were controlled by the CaMC35S promoter and had a trasnit peptide to target the protein to the chloroplast.
First and second regrowth cycles are the average of 6 and 9 sampled (n = 12 and 18), respectively. Spring is the mean of n = 4.

EXAMPLE 14

Increased Association with Mycorrhizal Fungi

A field trial was established as described in example 10 at Elora. The plant's roots were sampled in August. Roots were stained and examined for mycorrhizal fungi according to the method of McGonigle et al (1990). A random section of root was selected. The cross hair of the ocular was rotated to pass through the section perpendicular to the long axis of the root. If the cross hair contacted an arbuscle, vesicle or hypha, it was scored positive. This was repeated 100 times to determine the percentage data shown in Table 16.

TABLE 16

Association of mycorrhizal fungi with the roots of two alfalfa populations, with and without the ADH transgene, sampled at Elora in the year of transplanting.

| | Hypha (%) |
|---|---|
| Without ADH | 49 |
| With ADH | 80 |

EXAMPLE 15

Preparation of *Medicago sativa* Dual Transgenics

The inheritance and performance of alcohol dehydrogenase in combination with superoxide dismutase was assessed through paired cross-pollination between seven independent transgenic individuals. Cross-pollinations were made between one of two transgenic plants containing pADH3, H19-8 or H20-3; and one of four transgenic plants transformed with superoxide dismutase, N4 Mit MnSOD (pSOD1), N4 Chl MnSOD (pSOD4), S4 Chl MnSOD (pSOD4), N4 Chl FeSOD (pSOD10) or V4 Chl Fe SOD (pSOD10) where N4, S4 and V4 designate different alfalfa genotypes. 189 F1 progeny were grown from seed (Table 17).

TABLE 17

List of cross pollinations made between transgenic alfalfa plants expressing alcohol dehydrogenase and superoxide dismutase

| Cross | Family Code | Pollen donor | Number of Progeny |
|---|---|---|---|
| H19-8 × N4 Mit MnSOD | C11 | H19-8 | 32 |
| H20-3 × N4 Chl MnSOD | C17 | H20-3 | 28 |
| H20-3 × S4 Chl MnSOD | C26 | H20-3 | 21 |
| H19-8 × S4 Chl MnSOD | C30 | H19-8 | 18 |
| H20-3 × N4 Chl FeSOD | C01, C02 | Both | 34 |
| H20-3 × V4 Chl FeSOD | C27, C28 | Both | 31 |
| H19-8 × V4 Chl FeSOD | C31, C32 | Total | 189 |

The presence of pADH 3, pSOD1, 4 or 10 in the parental and progeny plants was verified by PCR (FIG. 19) and Southern hybridization using primers and probes specific to pADH3 and each pSOD. Of the 189 individuals assessed, 22.75% (43/189) were found to have inherited both parental transgenes. The remaining 77.25 inherited either one of the parental transgenes or neither transgene.

A field trial of all F1 progeny was established at Elora and New Liskeard. Individual rooted cuttings were transplanted into a randomized split plot design with three or four replicates of each family. Plot size was 1×1.5 m. The plants are analyzed for root and crown growth in the year of transplanting, for winter survival and yield in subsequent years.

Similar cross pollinations have been made among other primary transgenic alfalfa plants with glutathione reductase and superoxide dismutase in various combinations.

The progeny with the transgenes have larger root mass than those without the transgenes.

All citations are herein incorporated by reference.

Although the invention has been described with preferred embodiments, it is to be understood that modifications may be resorted to as will be apparent to those skilled in the art. Such modifications and variations are to be considered within the purview and scope of the present invention.

REFERENCES

Allen, R. D. (1995). Dissection of oxidative stress tolerance using transgenic plants. Plant Physiol 107: 1049–1054.

Asada, K. (1992). Ascorbate peroxidase—a hydrogen peroxide-scavenging enzyme in plants. Physiologia Plantarum 85: 235–241.

Ausubel, F. M., Roger, B., Kingston, R E., Moore, D. D., Seidman, J. G., Smith, J. A., and Struhl, K. Eds. 1991. Current Protocols In Molecular Biology. Chapter 2.9. Green Publishing Associates and Wiley-Interscience, Toronto Canada.

Barnes, R F., D. A. Miller, and C. J. Nelson. (1995). Forages. Vol 1. An Introduction to Grassland Agriculture. Iowa State University Press, Ames, Iowa. p. 157–160.

Bingham, E. T., L. V. Hurley, D. M. Kaatz and J. W. Saunders (1975). Breeding alfalfa which regenerates from callus tissue in culture. Crop Science 15. 719–721.

Boerjan, W., M. Cevera, M. Delarue, T. Beeckman, W. Dewitte, C. Bellini, M. Caboche, H. Van Onckeler, M van Montagu, and D. Inze (1995) superroot, a recessive mutation in Arabidopsis, confers auxin overproduction. Plant Cell 7: 1405–1419

Bowler, C., D. Inze and M. van Montagu (1992). Superoxide dismutase and stress tolerance. Annual Review of Plant Physiology and Plant Molecular Biology 43: 83–116.

Bowler, C., L. Slooten, S. Vandenbranden, R de Rycke, J. Botterman, C. Sybesma, M. van Montagu and D. Inze (1991). Manganese superoxide dismutase can reduce cellular damage mediated by oxygen radicals in transgenic plants. Embo J 10: 1723–1732.

Bowler, C., W. van Camp, M. van Montagu and D. Inze (1994). Superoxide dismutase in plants. Critical Reviews in Plant-Sciences 13: 199–218.

Bowley, S. R. and B. D. McKersie (1990). Relationships among freezing, low temperature flooding, and ice encasement tolerance in alfalfa. Can J Plant Science 70: 227–235.

Bowley, S. R. G. A. Kielly, K. Anandarajah, B. D. McKersie and T. Senaratna (1993). Field evaluation following two cycles of backcross transfer of somatic embryogenesis to commercial alfalfa germiplasm. Canadian Journal of Plant Science 73: 131–137.

Bradford, M. M. (1976). A rapid and sensitive method for the quantitation of microgram quantities of protein utilizing the principle of protein-dye binding. Analytical Biochemistry 72: 248–254.

Chang, C. and E. M. Meyerowitz (1986) Molecular cloning and DNA sequence of the Arabidopsis thaliana alcohol dehydrogenase. Proc Nat Acad Sci (USA) 83: 1408–1412

Chen, Z., H. Silva and D. F. Klessig (1993). Active oxygen species in the induction of plant systemic acquired resistance by salicylic acid. Science 262: 1883–1886.

D'Halluin, K. J. Botterman, and W. De Greef (1990) Engineering of herbicide-resistant alfalfa and evaluation under field conditions. Crop Sci. 30:866–871

De Block, M., et al. (1987) Engineering herbicide resistance in plants by expression of a detoxifying enzyme. EMBO J 6:2513–2518

De Marco, A. and K A. Roubelakis-Angelakis (1996). The complexity of enzymic control of hydrogen peroxide concentration may affect the regeneration potential of plant protoplasts. Plant Physiol. 110: 137–145.

Debaere R. et al. (1987) Vectors for cloning in plant cells. Methods Enzymol. 153: 277–292

Dellaporta, S. L. et al. (1983) A plant minipreparation: Version II. Plant Molecular Biology Reporter.

Fahrendorf, T., W. T. Ni, B. S. Shorrosh and R A. Dixon (1995). Stress responses in alfalfa (Medicago sativa L). 19. Transcriptional activation of oxidative pentose phosphate pathway genes at the onset of the isoflavonoid phytoalexin response. Plant Mol Biol 28: 885–900.

Foyer, C. (1993). Ascorbic acid. IN: R. G. Alscher and J. L. Hess (eds)_Antioxidants in Higher Plants. CRC Press, Boca Raton. pp. 31–58.

Foyer, C. H., P. Descourvieres and K. J. Kunert (1994). Protection against oxygen radicals: an inportant defence mechanism studied in transgenic plants. Plant, Cell and Environment 17: 507–523.

Gonzalez-Reyes, J. A., F. J. Alcain, J. A. Caler, A. Serrano, F. Cordoba and P. Navas. ( 1995). Stimulation of onion root elongation by ascorbate and ascorbate free radical in *Allium cepa* L. Protoplasma 184:31–35.

Gupta, A. S., J. L. Heinen, A. S. Holaday, J. J. Burke and R. D. Allen (1993). Increased resistance to oxidative stress in transgenic plants that overexpress chloroplastic Cu/Zn superoxide dismutase. Proceedings of the National Academy of Sciences of the United States of America 90: 1629–1633.

Gupta, A. S., R P. Webb, A. S. Holaday and R D. Allen (1993). Overexpression of superoxide dismutase protects plants from oxidative stress. Induction of ascorbate peroxidase in superoxide dismutase-overexpressing plants. Plant Physiology 103: 1067–1073.

Harourt, D., M. Van Montagu and D. Inze. (1993). Redox-activated expression of the cytosolic cooper/zinc superoxide dismutase gene in Nicotiana. Proc. Natl. Acad. Sci. USA. 90:3103–3112.

Hanson, A. A., D. K. Barnes, and R. R. Hill (1988) Alfalfa and Alfalfa Improvement. American Society of Agronomy, Madison, Wisc. pp. 195–228, 423–426.

Herouart, D., C. Bowler, H. Willekens, W. van Camp, L. Slooten, M. van Montagu, and D. Inze (1993). Genetic engineering of oxidative stress resistance in higher plants. Philosophical Transactions of the Royal Society of London. Series B, Biological Sciences 342: 235–240.

Hidalgo, A., G. Garcia-Herdugo, J. A. Gonzalez-Reyes, D. J. MorrS and P. Navas. (1991). Ascorbate free radical stimulates onion root growth by increasing cell elongation. Bot. Gaz. 152(3):282–288.

Ho, L. C. (1998) Metabolism and compartmentation of imported sugars in sink organs in relation to sink strength. Annual Review of Plant Physiology and Plant Molecular Biology 39: 355–378.

Huner, N. P. A., D. P. Maxwell, G. R Gray, L. V. Savitch, M. Krol, A. G. Ivanov and S. Falk (1996). Sensing environmental temperature change through imbalances between energy supply and energy consumption: Redox state of photosystem II. Physiol Plant 98: 358–364.

Maxwell, D. P., D. E. Laudenbach and N. P. A. Huner (1995). Redox regulation of light-harvesting complex II and cab mRNA abundance in Dunaliella salina. Plant Physiol 109: 787–795.

McKersie, B. D. and Y. V. Leshem (1994). *Stress and stress coping in cultivated plants.* Dordrecht, Netherlands, Kluwer Academic Publishers.

McKersie, B. D., S. R. Bowley, E. Hacjanto and O. Leprince (1996). Water-deficit tolerance and field performance of transgenic alfalfa overexpressing superoxide dismutase. Plant Physiol 111: 1177–1181.

McKersie, B. D., Y. R. Chen, M. deBeus, S. R. Bowley, C. Bowler, D. Inzé, K. D'Halluin and J. Botterman (1993). Superoxide dismutase enhances tolerance of freezing stress in transgenic alfalfa (Medicago sativa L.). Plant Physiology 103: 1155–1163.

McKersie, B. D., J. Murnaghan and S. R Bowley. (1997) Manipulating freezing tolerance in transgenic plants. Acta Physiol. Plant 19: 485495

Moore, D. J., P. Navas, C. Penel and F. J. Castillo. (1986). Auxin-stimulated NADH Oxidase (Semidehydroascorbate Reductase) of Soybean Plasma Membrane: Role in Acidification of Cytoplasm? Protoplasma 133:195–197.

Murashige, T. and F. Skoog (1962). A revised medium for rapid growth and bioassays with tobacco cultures. Physiologia Plantarum 15: 473–479.

Navas, P. and C. G. mez-Diaz. (1995). Ascorbate free radical and its role in growth control. Protoplasma. 184:8–13.

OMAFRA (1997) Field Crop Recommendations. Publication 296. Ontario Ministry of Agiculture and Food.

Payton, P., R. D. Allen, N. Trolinder and A. S. Holaday (1997). Over-expression of chloroplast-targeted Mn superoxide dismutase in cotton (*Gossypium hirsuturn* L., cv. Coker 312) does not alter the reduction of photosynthesis after short exposures to low temperature and high light intensity. Photosynth Res 52: 233–244.

Perl, A., R. Perl Treves, S. Galili, D. Aviv, E. Shalgi, S. Malkin and E. Galun (1993). Enhanced oxidative-stress defense in transgenic potato expressing tomato Cu,Zn superoxide dismutases. Theoretical and Applied Genetics 85: 568–576.

Pitcher, L. H., E. Brennan, A. Hurley, P. Dunsmair, J. M. Tepperman and B. A. Zilinskas (1991). Overproduction of petunia chloroplastic copper/zinc superoxide dismutase does not confer ozone tolerance in transgenic tobacco. Plant Physiology 97: 452–455.

Prasad, T. K., M. D. Anderson, B. A. Martin and C. R Stewart (1994). Evidence for chilling-induced oxidative stress in maize seedliongs and a regulatory role for hydrogen peroxide. The Plant Cell 6: 65–74.

Price, A. H., A. Taylor, S. J. Ripley, A. Griffiths, A. J. Trewavas and M. R. Knight (1994). Oxidative signals in tobacco increase cytosolic calcium. Plant Cell6: 1301–1310.

Rayle, D. L. and R. E. Cleland (1992) The acid growth theory of auxin-induced cell elongation is alive and well. Plant Physiol. 99:1271–1274.

Regad, F., C. Herve and O. Marinx. (1995). The tefl box, a ubiquitous cis-acting element involved in the activation of plant genes that are highly expressed in cycling cells. Mol. Gen. Genet. 248:703–711.

Robertson, D., D. R. Davies, C. Gerrish, S. C. Jupe and G. P. Bolwell (1995). Rapid changes in oxidative metabolism as a consequence of elicitor treatment of sugpension-cultured cells of French bean (*Phaseolus vulgaris L*). Plant Mol Biol 27: 59–67.

Scandalios, J. G. (1993). Oxygen stress and superoxide dismutases. Plant Physiology 101: 7–12.

Seo, M., S. Akaba, T. Oritani, M. Delarue, C. Bellini, M. Caboche, and T. Koshiba (1998) Higher activity of an adehyde oxidase in the auxin-overproducing superroot mutant of *Arabidopsis thaliana*. Plant Physiol 116:687–693.

Shetty, K. and B. D. McKersie (1993). Proline, thioproline and potassium mediated stimulation of somatic embryogenesis in alfalfa (Medicago sativa L.). Plant Science 88: 185–193.

Slekar, K. H., D. J. Kosman and V. C. Culotta (1996). The Yeast Cooper/Zinc Superoxide Dismutase and the Pentose Phosphate Pathway Play Overlapping Roles in Oxidative Stress Protection. The Journal of Biological Chemistry, Vol. 271(46):2883–28836.

Sonnewald, U., M. R Hajirezaci, J. Kossmann, A. Heyer, R N. Trethewey, and L. Willmitzer (1997) Increased potato tuber size resulting from apoplastic expression of a yeast invertase. Nat Biotechnol 15:794–797.

Steponkus, P. L. and F. O. Lanphear (1967). Refinement of the triphenyl tetrazolium chloride method of determining cold injury. Plant Physiol. 42: 423–1426.

Tepperman, J. M. and P. Dunsmuir (1990). Transformed plants with elevated level of chloroplastic SOD are not more resistant to superoxide toxicity. Plant Molecular Biology 14: 501–511.

Thompson, J. E., R. L. Legge and R F. Barber (1987). The role of free radicals in senescence and wounding. New Phytologist 105: 317–344.

Toledo, I., A. A. Noronha-Dutra and W. Hansberg. (1991). Loss of NAD(P)—Reducing Power and Glutathione Disulfide Excretion at the Start of Induction of Aerial Gowth in *Neurospora crassa*. J. of Bacteriaology. 173(10): 3243–3249.

Van Camp, W., et al. (1996). Enhancement of oxidative stress tolerance in transgenic tobacco plants overproducing Fe-superoxide dismutase in chloroplasts. Plant Physiol 112: 1703–1714

Van Camp, W., H. Willekens, C. Bowler, M. v. Montagu, D. Inze, P. Reupold Popp, H. Sandermann, Jr. and C. Langebartels (1994). Elevated levels of superoxide dismutase protect transgenic plants against ozone damage. Bio Technology 12: 165–168.

Van Camp, W., K. Capiau, M. Van Montagu, D. Inze and L. Slooten (1996). Enhancement of oxidative stress tolerance in transgenic tobacco plants overproducing Fe-superoxide dismutase in chloroplasts. Plant Physiol. 112. 1703–1714.

van Miltenburg, R. Ruger, B., Grunewald-Janho, S., Leons, M., Schroder, C., Eds. 1995. The Dig System User's Guide for Filter Hybridization. Boehringer Mannheim GmbH, Biochemia, Germany.

Velten, J., L. Velten, R Hain and J Schell (1984) Isolation of a dual promoter fragment from the Ti plasmid of *Agrobacterium tumefaciens*. EMBO J 3:2723–2730

What is claimed is:

1. A method of increasing weight of a storage organ of a plant, said method comprising:
   i) transforming said plant with at least one nucleic acid molecule comprising a regulatory element preferentially active in a root or storage organ in operative association with at least one transgene that encodes a plant alcohol dehydrogenase, to produce a transformed plant;
   ii) selecting said transformed plant comprising said at least one transgene;
   iii) growing said transformed plant to produce said plant exhibiting increased weight of said storage organ when compared to an equivalent non-transformed plant, wherein said transformed plant and said equivalent non-transformed plant are grown under similar conditions.

2. The method of claim 1, wherein said plant alcohol dehydrogenase is from *Arabidopsis thaliana*.

3. A transgenic plant or progeny thereof, produced by the method of claim 1.

4. A transgenic plant cell produced by the method of claim 1.

5. A transgenic seed produced by the method of claim 1.

6. The method of claim 1, wherein said step of growing (step (iii)) said transformed plant produces increased herbage yield when compared to an equivalent non-transformed plant, wherein said transformed plant and said equivalent non-transformed plant are grown under similar conditions.

7. The method of claim 1, further comprising the steps of:
   iv) transforming a second plant with a second transgene that encodes an enzyme selected from the group consisting of glutathione reductase, monodehydroascorbate reductase, mitochondrial alternative oxidase, NADH oxidase, NADPH oxidase, superoxide dismutase, ascorbate peroxidase and dehydroxyascorbate reductase to produce a second transformed plant;
   v) selecting said second transformed plant comprising said second transgene;
   vi) growing said second transformed plant;
   vii) cross-pollinating said transformed plant with said second transformed plant to produce a dual transgenic plant;
   viii) selecting said dual transgenic plant; and
   ix) growing said dual transgenic plant exhibiting increased weight of said storage organ when compared to said equivalent non-transformed plant, wherein said dual transgenic plant and said equivalent non-transformed plant are grown under similar conditions.

8. The transgenic plant or progeny thereof, of claim 3, wherein said plant is a perennial plant.

9. The transgenic plant or progeny thereof, of claim 3, wherein said plant is an annual plant.

10. A transgenic plant or progeny thereof, produced by the method of claim 7.

11. A transgenic plant cell produced by the method of claim 7.

12. A transgenic seed produced by the method of claim 7.

13. The method of claim 7, wherein said step of growing (step (ix)) said dual transgenic plant produces increased herbage yield when compared to an equivalent non-transformed plant, wherein said transformed plant and said equivalent non-transformed plant are grown under similar conditions.

14. The transgenic plant according to claim 8 wherein said perennial plant is selected from the group consisting of strawberries, raspberries, grapevine, apple, roses, orchardgrass, bromegrass, timothy, ryegrass, fescue, alfalfa, clover, birdsfoot trefoil, turfgrass, bentgrass and bluegrass.

15. The transgenic plant according to claim 9 wherein said annual plant is a winter annual plant or a root crop.

16. The transgenic plant or progeny thereof, of claim 10, wherein said plant is a perennial plant.

17. The transgenic plant or progeny thereof, of claim 10, wherein said plant is an annual plant.

18. The transgenic plant according to claim 15 wherein said annual plant is selected from the group consisting of Brassica spp., wheat, barley, oats, rye, canola, maize, rice, soybean, potatoes, carrots, turnips, ginseng, sugarbeet, cassava, and Phaseolus spp.

19. The transgenic plant according to claim 16 wherein said perennial plant is selected from the group consisting of strawberries, raspberries, grapevine, apple, roses, orchardgrass, bromegrass, timothy, ryegrass, fescue, alfalfa, clover, birdsfoot trefoil, turfgrass, bentgrass and bluegrass.

20. The transgenic plant according to claim 17 wherein said annual plant is a winter annual plant or a root crop.

21. The transgenic plant according to claim 20 wherein said annual plant is selected from the group consisting of Brassica spp., wheat, barley, oats, rye, canola, maize, rice, soybean, potatoes, carrots, turnips, ginseng, sugarbeet, cassava, and Phaseolus spp.

22. A vector comprising a regulatory element preferentially active in a root or storage organ in operative association with at least one transgene, said transgene in oprative association with a 3' untranslated region, wherein said at least one transgene encodes a plant alcohol dehydrogenase.

23. The vector of claim 22, wherein said a plant alcohol dehydrogenase is from *Arabidopsis thaliana*.

24. The vector of claim 22, wherein said regulatory element is root specific.

25. A transgenic plant comprising the vector of claim 22.

26. A transgenic plant cell comprising the vector of claim 22.

27. A transgenic seed comprising the vector of claim 22.

28. A method to overexpress a plant alcohol dehydrogenase in a plant comprising:
   i) transforming said plant with said vector of claim 22 to produce a transformed plant;
   ii) selecting said transformed plant comprising a transgene encoding said plant alcohol dehydrogenase; and
   iii) growing said transformed plant and overexpressing said plant alcohol dehydrogenase.

29. A method to overexpress an alcohol dehydrogenase from *Arabidopsis thaliana* in a plant comprising:
   i) transforming said plant with said vector of claim 23 to produce a transformed plant;

ii) selecting said transformed plant comprising a transgene encoding said alcohol dehydrogenase from *Arabidopsis thaliana*; and iii) growing said transformed plant and overexpressing said alcohol dehydrogenase from *Arabidopsis thaliana*.

30. The transgenic plant of claim 25, wherein said plant is a perennial plant.

31. The transgenic plant of claim 25, wherein said plant is an annual plant.

32. The transgenic plant according to claim 30 wherein said perennial plant is selected from the group consisting of strawberries, raspberries, grapevine, apple, roses, orchardgrass, bromegrass, timothy, ryegrass, fescue, alfalfa, clover, birdsfoot trefoil, turfgrass, bentgrass and bluegrass.

33. The transgenic plant according to claim 26 wherein said perennial plant is selected from the group consisting of strawberries, raspberries, grapevine, apple, roses, orchardgrass, bromegrass, timothy, ryegrass, fescue, alfalfa, clover, birdsfoot trefoil, turfgrass, bentgrass and bluegrass.

34. The transgenic plant according to claim 31 wherein said annual plant is a winter annual plant or a root crop.

35. The transgenic plant according to claim 27 wherein said annual plant is a winter annual plant or a root crop.

36. The transgenic plant according to claim 34 wherein said annual plant is selected from the group consisting of Brassica species (spp.), wheat, barley, oats, rye, canola, maize, rice, soybean, potatoes, carrots, turnips, ginseng, sugarbeet, cassava, and Phaseolus spp.

37. The transgenic plant according to claim 35 wherein said annual plant is selected from the group consisting of Brassica spp., wheat, barley, oats, rye, canola, maize, rice, soybean, potatoes, carrots, turnips, ginseng, sugarbeet, cassava, and Phaseolus spp.

38. A method of increasing tolerance to environmental stress of a plant, said method comprising:
  i) transforming said plant with at least one nucleic acid molecule comprising a regulatory element preferentially active in a root or storage organ in operative association with at least one transgene that encodes a plant alcohol dehydrogenase, to produce a transformed plant;
  ii) selecting said transformed plant comprising said at least one transgene;
  iii) growing said transformed plant to produce said plant, said plant exhibiting increased tolerance to environmental stress when compared to an equivalent non-transformed plant, wherein said transformed plant and said equivalent non-transformed plant are grown under similar conditions.

39. The method of claim 38, wherein said environmental stress is flooding, freezing, desiccation, or drought or a combination thereof.

40. The method of claim 38, wherein said plant alcohol dehydrogenase is from *Arabidopsis thaliana*.

41. The method of claim 38, further comprising the steps of:
  iv) transforming a second plant with a second transgene that encodes an enzyme selected from the group consisting of glutathione reductase, monodehydroascorbate reductase, mitochondrial alternative oxidase, NADH oxidase, NADPH oxidase, superoxide dismutase, ascorbate peroxidase and dehydroxyascorbate reductase to produce a second transformed plant;
  v) selecting said second transformed plant comprising said second transgene;
  vi) growing said second transformed plant; and
  vii) cross-pollinating said transformed plant with said second transformed plant to produce a dual transgenic plant exhibiting increased tolerance to environmental stress when compared to an equivalent non-transformed plant, wherein said dual transgenic plant and said equivalent non-transformed plant are grown under similar conditions.

42. The method of claim 41, wherein said environmental stress is flooding, freezing, desiccation, drought, or a combination thereof.

43. A method of increasing weight of a storage organ of a plant, said method comprising:
  i) transforming said plant with at least one transgene that encodes an ascorbate peroxidase, to produce a transformed plant;
  ii) selecting said transformed plant comprising said at least one transgene;
  iii) growing said transformed plant exhibiting increased weight of said storage organ when compared to an equivalent non-transformed plant, wherein said transformed plant and said equivalent non-transformed plant are grown under similar conditions;
  iv) transforming a second plant with a second transgene that encodes an enzyme selected from the group consisting of glutathione reductase, monodehydroascorbate reductase, mitochondrial alternative oxidase, NADH oxidase, NADPH oxidase, superoxide dismutase, and dehydroxyascorbate reductase to produce a second transformed plant;
  v) selecting said second transformed plant comprising said second transgene;
  vi) growing said second transformed plant;
  vii) cross-pollinating said transformed plant with said second transformed plant to produce a dual transgenic plant;
  viii) selecting said dual transgenic plant; and
  ix) growing said dual transgenic plant exhibiting increased weight of said storage organ when compared to said equivalent non-transformed plant, wherein said dual transgenic plant and said equivalent non-transformed plant are grown under similar conditions.

44. A transgenic plant or progeny thereof, produced by the method of claim 43.

45. A transgenic plant cell produced by the method of claim 43.

46. A transgenic seed produced by the method of claim 43.

47. The method of claim 43, wherein said step of growing (step (ix)) said dual transgenic plant produces increased herbage yield when compared to an equivalent non-transformed plant, wherein said transformed plant and said equivalent non-transformed plant are grown under similar conditions.

48. The transgenic plant or progeny thereof, of claim 44, wherein said plant is a perennial plant.

49. The transgenic plant or progeny thereof, of claim 44, wherein said plant is an annual plant.

50. The transgenic plant according to claim 48 wherein said perennial plant is selected from the group consisting of strawberries, raspberries, grapevine, apple, roses, orchardgrass, bromegrass, timothy, ryegrass, fescue, alfalfa, clover, birdsfoot trefoil, turfgrass, bentgrass and bluegrass.

51. The transgenic plant according to claim 49 wherein said annual plant is a winter annual plant or a root crop.

52. The transgenic plant according to claim 51 wherein said annual plant is selected from the group consisting of Brassica spp., wheat, barley, oats, rye, canola, maize, rice, soybean, potatoes, carrots, turnip, ginseng, sugarbeet, cassava, and Phaseolus spp.

53. A method of increasing tolerance to environmental stress of a plant, said method comprising:

i) transforming said plant with at least one transgene that encodes an ascorbate peroxidase, to produce a transformed plant;

ii) selecting said transformed plant comprising said at least one transgene;

iii) growing said transformed plant exhibiting increased tolerance to environmental stress when compared to an equivalent non-transformed plant, wherein said transformed plant and said equivalent non-transformed plant are grown under similar conditions;

iv) transforming a second plant with a second transgene that encodes an enzyme selected from the group consisting of glutathione reductase, monodehydroascorbate reductase, mitochondrial alternative oxidase, NADH oxidase, NADPH oxidase, superoxide dismutase, and dehydroxyascorbate reductase to produce a second transformed plant;

v) selecting said second transformed plant comprising said second transgene;

vi) growing said second transformed plant; and vii) cross-pollinating said transformed plant with said second transformed plant to produce a dual transgenic plant exhibiting increased tolerance to environmental stress when compared to said equivalent non-transformed plant, wherein said dual transgenic plant and said equivalent non-transformed plant are grown under similar conditions.

54. The method of claim 53, wherein said environmental stress is flooding, freezing, desiccation, drought, or a combination thereof.

55. A dual transgenic plant, or progeny thereof, comprising:

i) at least one transgene that encodes an alcohol dehydrogenase; and ii) a second transgene that encodes an enzyme selected from the group consisting of glutathione reductase, monodehydroascorbate reductase, mitochondrial alternative oxidase, NADH oxidase, NADPH oxidase, superoxide dismutase, ascorbate peroxidase and dehydroxyascorbate reductase.

56. A dual transgenic plant cell comprising:

i) at least one transgene that encodes an alcohol dehydrogenase; and ii) a second transgene that encodes an enzyme selected from the group consisting of glutathione reductase, monodehydroascorbate reductase, mitochondrial alternative oxidase, NADH oxidase, NADPH oxidase, superoxide dismutase, ascorbate peroxidase and dehydroxyascorbate reductase.

57. A dual transgenic plant seed comprising:

i) at least one transgene that encodes an alcohol dehydrogenase; and ii) a second transgene that encodes an enzyme selected from the group consisting of glutathione reductase, monodehydroascorbate reductase, mitochondrial alternative oxidase, NADH oxidase, NADPH oxidase, superoxide dismutase, ascorbate peroxidase and dehydroxyascorbate reductase.

58. A method of increasing weight of a storage organ of a plant, said method comprising:

i) transforming said plant with at least one transgene that encodes a plant alcohol dehydrogenase, to produce a transformed plant;

ii) selecting said transformed plant comprising said at least one transgene;

iii) growing said transformed plant to produce said plant exhibiting increased weight of said storage organ when compared to an equivalent non-transformed plant, wherein said transformed plant and said equivalent non-transformed plant are grown under similar conditions.

59. A method of increasing weight of a storage organ of a plant, said method comprising:

i) transforming said plant with at least one nucleic acid molecule comprising a regulatory element preferentially active in a root or storage organ in operative association with at least one transgene that encodes a plant alcohol dehydrogenase, to produce a transformed plant;

ii) selecting said transformed plant comprising said at least one transgene;

iii) growing said transformed plant to produce said plant exhibiting increased weight of said storage organ when compared to an equivalent non-transformed plant, wherein said transformed plant and said equivalent non-transformed plant are grown under similar conditions.

60. A method of increasing weight of a storage organ of a plant, said method comprising:

i) transforming said plant with at least one nucleic acid molecule comprising a TR2' promoter in operative association with at least one transgene that encodes an alcohol dehydrogenase, to produce a transformed plant;

ii) selecting said transformed plant comprising said at least one transgene;

iii) growing said transformed plant to produce said plant exhibiting increased weight of said storage organ when compared to an equivalent non-transformed plant, wherein said transformed plant and said equivalent non-transformed plant are grown under similar conditions.

61. A method of increasing weight of a storage organ of a plant, said method comprising:

i) transforming said plant with at least one nucleic acid molecule comprising a TR2' promoter in operative association with at least one transgene that encodes a plant alcohol dehydrogenase, to produce a transformed plant;

ii) selecting said transformed plant comprising said at least one transgene;

iii) growing said transformed plant to produce said plant exhibiting increased weight of said storage organ when compared to an equivalent non-transformed plant, wherein said transformed plant and said equivalent non-transformed plant are grown under similar conditions.

62. A method of increasing weight of a storage organ of a plant, said method comprising:

i) transforming said plant with at least one nucleic acid molecule comprising a regulatory element preferentially active in a root or storage organ in operative association with at least one transgene that encodes an alcohol dehydrogenase from *Arabidopsis thaliana*, to produce a transformed plant;

ii) selecting said transformed plant comprising said at least one transgene;

iii) growing said transformed plant to produce said plant exhibiting increased weight of said storage organ when compared to an equivalent non-transformed plant, wherein said transformed plant and said equivalent non-transformed plant are grown under similar conditions.

\* \* \* \* \*

UNITED STATES PATENT AND TRADEMARK OFFICE
CERTIFICATE OF CORRECTION

PATENT NO.    : 6,518,486 B1
DATED         : February 11, 2002
INVENTOR(S)   : Bryan D. McKersie et al.

It is certified that error appears in the above-identified patent and that said Letters Patent is hereby corrected as shown below:

<u>Title page,</u>
Item [60], provisional application serial number should read -- 60/089,187 --.

Signed and Sealed this

Twelfth Day of August, 2003

JAMES E. ROGAN
*Director of the United States Patent and Trademark Office*

SEQUENCE LISTING

<160> NUMBER OF SEQ ID NOS:   6

<210> SEQ ID NO 1
<211> LENGTH: 15
<212> TYPE: DNA
<213> ORGANISM: Artificial
<220> FEATURE:
<223> OTHER INFORMATION: Synthetic

<400> SEQUENCE: 1
atcggatcca tgtct                                                      15

<210> SEQ ID NO 2
<211> LENGTH: 21
<212> TYPE: DNA
<213> ORGANISM: Artificial
<220> FEATURE:
<223> OTHER INFORMATION: Synthetic

<400> SEQUENCE: 2
agctgtgctc gacgttgtca g                                               21

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
ggtgggcgaa gaactccagc a                                               21

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
agctgtgctc gacgttgtca c                                               21

<210> SEQ ID NO 5
<211> LENGTH: 18
<212> TYPE: DNA
<213> ORGANISM: Artificial
<220> FEATURE:
<223> OTHER INFORMATION: Synthetic

<400> SEQUENCE: 5
gagcagacgg accttagc                                                   18

<210> SEQ ID NO 6
<211> LENGTH: 18
<212> TYPE: DNA
<213> ORGANISM: Artificial

```
<220> FEATURE:
<223> OTHER INFORMATION: Synthetic

<400> SEQUENCE: 6
agaaaccaaa gggtcctg                                              18
```